United States Patent
Lampotang et al.

[19]

[11] Patent Number: 6,131,571

[45] Date of Patent: Oct. 17, 2000

[54] VENTILATION APPARATUS AND ANESTHESIA DELIVERY SYSTEM

[75] Inventors: Samsun Lampotang; Joachim S. Gravenstein; Johannes Hugo Maria van Oostrom, all of Gainesville, Fla.

[73] Assignee: University of Florida, Gainesville, Fla.

[21] Appl. No.: 08/848,339

[22] Filed: Apr. 30, 1997

[51] Int. Cl.[7] .................................................. A61M 16/00
[52] U.S. Cl. ................ 128/204.21; 128/204.18; 128/204.23
[58] Field of Search ................ 728/204.21, 205.18, 728/203.28, 205.12, 204.28, 203.12, 203.14, 205.25, 204.23, 204.24, 205.19, 205.11, 202.27

[56] References Cited

U.S. PATENT DOCUMENTS

| | | | |
|---|---|---|---|
| 3,730,180 | 5/1973 | Davison | 128/204.24 |
| 4,340,044 | 7/1982 | Levy et al. | 128/205.24 |
| 5,103,814 | 4/1992 | Maheo | 128/204.23 |
| 5,116,088 | 5/1992 | Bird | 128/202.27 |
| 5,429,123 | 7/1995 | Shefler et al. | 128/205.25 |
| 5,497,767 | 3/1996 | Olsson et al. | 128/205.13 |
| 5,645,054 | 7/1997 | Cotner et al. | 128/204.21 |
| 5,664,563 | 9/1997 | Schroeder et al. | 128/204.25 |
| 5,678,540 | 10/1997 | Nock et al. | 128/205.13 |
| 5,694,926 | 12/1997 | De Varies et al. | 128/205.24 |

OTHER PUBLICATIONS

Br. J. Anaesth. (1986) 58, 1161–1166, C.E.W. Hahn, et al., "A Microprocessor–Controlled Anaesthetic Vaporizer".
Br. J. Anaesth. (1986), 58, 1041–1047, E. Palayiwa, et al., "A Microprocessor–Controlled Gas Mixing Device".
Br. J. Anaesth. (1983), 55, 1053, J.A.S. Ross, et al., "Servo–Controlled Closed–Circuit Anaesthesia".
Anesthesiology 49:310–318, 1978, Jeffrey B. Cooper, Ph.D., et al., "A New Anesthesia Delivery System".
IEEE Transactions on Biomedical Engineering, vol. BME–34, No. 6, Jun. 1987, R. Gilbert Ritchie, et al., "Closed–Loop Control Of An Anethesia Delivery System: Development And Animal Testing".
Anesthesiology, Jul.–Aug. 1961. Peter J. Roffey, et al., "An Assessment Of The Revell Circulator".
Anesthesiology, 70:999–1007, 1989, Robert G. Loeb, M.D., et al., "The Utah Anesthesia Workstation".
Br. J. Anaesth. (1989) 62, 445–455, M.K. Sykes, et al., "A New Microprocessor–Controlled Anaesthetic Machine".

*Primary Examiner*—John G. Weiss
*Assistant Examiner*—V. Srivastava
*Attorney, Agent, or Firm*—Needle & Rosenberg, P.C.

[57] ABSTRACT

A combination ventilation apparatus and anesthesia delivery system comprises a circulation loop within which oxygen and air or other clinical gas, or a mixture of air, oxygen, nitrous oxide or other clinical gas and anesthetics, are circulated by a variable speed centrifugal blower to a Y-piece which connects the circulation loop to an endotracheal tube or other airway device communicating with a patient. A proportional flow control valve is operative to actively control the pressure or flow at the Y-piece in response to signals from pressure or flow sensors which are positioned to provide measurements representative of the actual pressure and flow conditions within the patient's lungs. Constant circuit volume is maintained by computer control of gas make-up valves in response to the movement of a weighted bellows located between the proportional flow control valve and centrifugal blower.

88 Claims, 5 Drawing Sheets

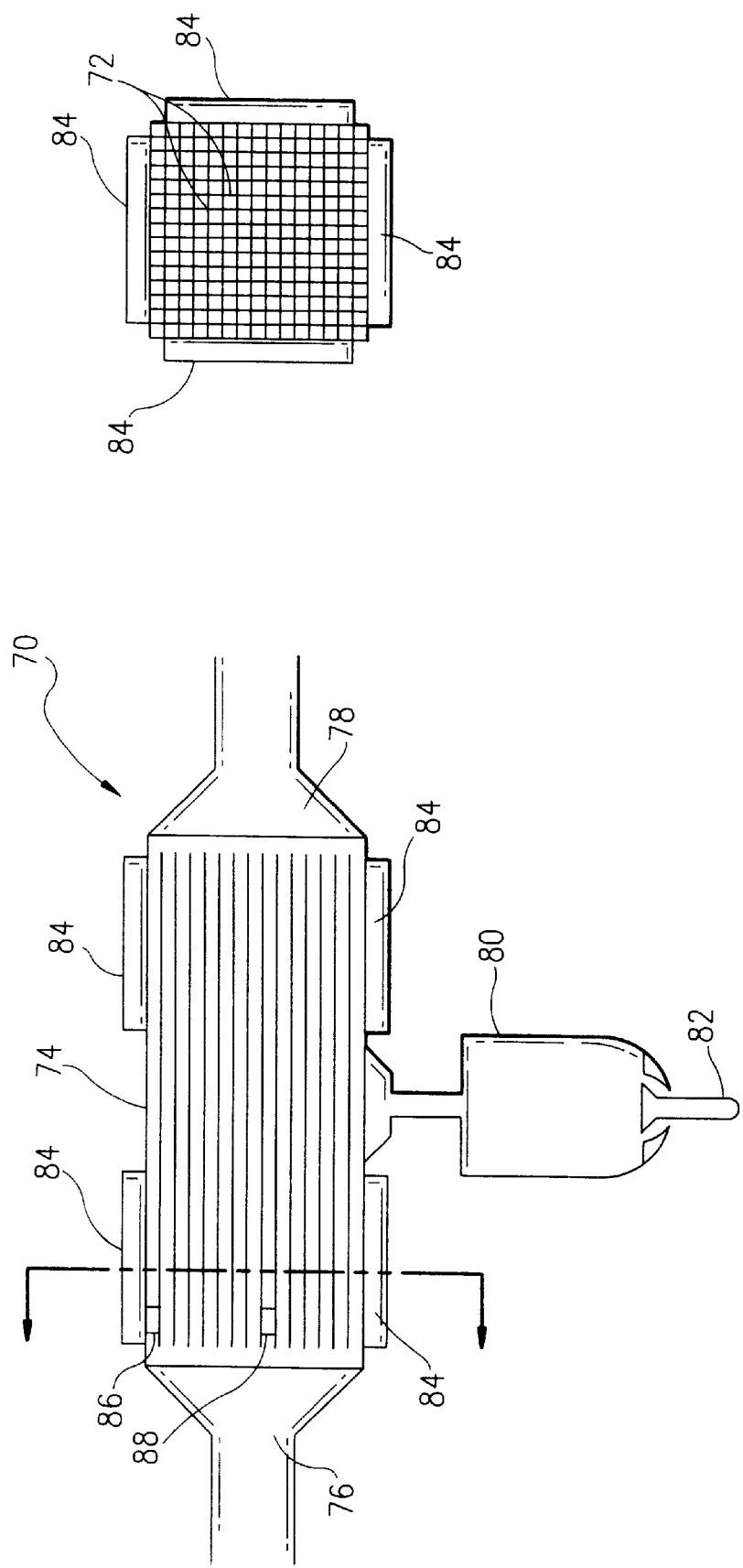

VENTILATION APPARATUS AND ANESTHESIA DELIVERY SYSTEM

FIELD OF THE INVENTION

This invention relates to ventilation apparatus and anesthesia delivery systems, and, more particularly, to an apparatus functional as a ventilator and/or an inhalation anesthesia system which is capable of ventilating patients of all types including those with lungs having relatively stiff compliance, and which functions as an efficient, economic and user-friendly anesthesia delivery system.

BACKGROUND OF THE INVENTION

There are three types of anesthesia commonly utilized to perform surgical procedures including local, regional and general. Local anesthesia is administered via local drug injections directly into the effective tissues, while regional anesthesia is accomplished by injecting anesthetics into the tissues adjacent to the nerve supply of a specific region, thus anesthetizing the area of surgery. General anesthesia depresses the central nervous system and is preferred for major operations. It is often induced with intravenous anesthetics such as non-volatile drugs, and maintained with inhalation (volatile) anesthetics. The most commonly used anesthetic gas is nitrous oxide, in combination with oxygen and an intravenous or volatile anesthetic such as isoflurane, halothane, enflurane, desflurane and sevoflurane. A 100% concentration of nitrous oxide is lethal to a patient, hence the need for intermixture with oxygen, and a volatile anesthetic is necessary because of a comparatively low potency of nitrous oxide.

The delivery of inhalation anesthetics to patients has been the subject of a great deal of development since surgical anesthetics were first introduced in 1846. Inhalation anesthetics are delivered to the patient by ventilation, which is a process distinct from anesthesia but acts as a convenient delivery medium. Ventilation itself is the process of bringing oxygen into the alveoli of the lungs, and washing out carbon dioxide from the lungs. Three types of ventilation are possible during inhalation anesthesia, including spontaneous, assisted or controlled. In spontaneous ventilation, the patient breathes at his or her own pace without any assistance from the anesthesiologist or ventilation machine, although some ventilation machines are capable of assisting the patient to reduce his or her work of breathing. Assisted ventilation, also known as manual ventilation or "handbagging," is performed by the anesthesiologist manually squeezing a breathing bag attached to the anesthesia breathing circuit to supplement the spontaneous ventilation of the patient.

During general anesthesia, where the patient is essentially paralyzed by neuromuscular blocking agents and the anesthetic gas, mechanically controlled ventilation is utilized to automatically ventilate the patient's lungs. Various modes of mechanical or automatic ventilation are currently used including closed-circuit, open-circuit, high frequency ventilation and continuous-flow apneic ventilation, among others. High frequency ventilation is characterized by the introduction of pulsed or intermittent, relatively small volumes of air into the patient's lungs. This mode of ventilation is especially useful in extracorporeal shock wave lithotripsy which is a non-invasive way of pulverizing kidney stones with focused shock wave energy. Continuous-flow apneic ventilation introduces high flow rates of gas via catheters inserted in the patient's bronchi, and relies on the continuous flow of gas to bring in oxygen and wash out carbon dioxide. Closed and open circuit ventilation are generally differentiated by whether or not the gas flow is completely recirculated to the patient (closed systems), or never recirculated for re-inhalation by the patient (open system) and variations in between (semi-closed, semi-open).

Although a number of inhalation anesthesia systems have been proposed, the most common commercial design employed in this country and much of the world consists of four main components, including: (1) an anesthesia machine, (2) an anesthesia ventilator, (3) an anesthesia circuit, and, (4) a scavenging system. The "anesthesia machine" is an assembly for the blending of air, helium and/or oxygen with nitrous oxide and one or more volatile anesthetics such as isoflurane, halothane, enflurane, desflurane and sevoflurane. The air, oxygen and nitrous oxide are intermixed within a common manifold containing rotameters which provide independent metering of each gas. The intermixed gases exit the manifold and are directed through a vaporizer, usually of the flow-over type, where the volatile anesthetic is added.

The gas mixture produced by the anesthesia machine enters the "anesthesia circuit" which is connected to the patient. A number of anesthesia circuits can be utilized, but many commercial designs employ a "circle" system for delivery of the gas mixture to a patient via a facemask fitted over the nose and mouth of a patient, or an endotracheal tube with which the patient is intubated. A circle anesthesia circuit includes a circulation loop having an inlet connected to the anesthesia machine, an outlet connected to the scavenging system and a Y-piece or other means of connection to the patient. The circulation loop carries an inspiratory valve which is a one-way valve allowing passage of the gas mixture to the patient, and an expiratory valve which is a one-way valve permitting passage of the gas exhaled by the patient. If the circle anesthesia circuit is operated in an "open" mode, gas exhaled from the patient is transmitted directly to a scavenging system for collection and disposal. In the closed or semi-closed mode of operation, all or part of the gas exhaled by the patient is recirculated within the circulation loop, and a carbon dioxide absorber is mounted therein to remove carbon dioxide from the gas flow before it is directed back to the patient.

Circle anesthesia circuits are normally equipped with a manual breathing bag which allows the anesthesiologist to manually ventilate the patient by squeezing the bag. Manual ventilation requires constant attention on the part of the anesthesiologist, and ties up at least one hand. To free the clinician's hand, once the anesthetic is safely under way, the anesthesia ventilator is connected to the circulation loop to provide for mechanical ventilation of the patient. In switching from manual to mechanical ventilation, a valve (e.g., a selector knob) in the system is manually operated to block the passage to the manual breathing bag, and interconnect the anesthesia ventilator with the circulation loop. Typically, an ascending bellows ventilator is incorporated in the anesthesia ventilator, which, under pressurization from gas supplied by the ventilator, is operative to alternately descend to inflate and ventilate the patient's lungs, and ascend passively from the build-up of exhaled gases from the patient. A ventilator exhaust valve is also provided to prevent overpressurization. During exhalation, after the bellows has fully ascended, the ventilator exhaust valve opens and allows the excess gases to spill into the scavenging system, so that there is no net buildup of pressure.

Efforts have been made to improve the operation of anesthesia delivery systems of the type described above, particularly in connection with incorporating electronic control features and data acquisition sensors. For example, sensors have been employed at the connection of the circuit to the patient for the determination of the inspired and exhaled gas concentrations during an anesthetic procedure. A feedback loop can be employed to control the introduction of new anesthetic into the breathing circuit dependent upon the concentration of anesthetic sensed by the sensors. Anesthesia delivery systems provide for "flushing" of the circuit by a high flow rate of oxygen in order to remove an undesirable concentration of carbon dioxide and/or anesthetics which may be present, or to compensate for loss of circuit volume following, e.g., a momentary disconnection.

Despite advances in anesthesia delivery systems, a number of problems remain which limit their efficiency, economic benefit, and, in some instances, impact adversely upon patients' safety. One pervasive problem with existing anesthesia delivery systems is that they deliver expensive anesthetic gases inefficiently and at flow rates much higher than necessary. In a high percentage of instances, less than 5% of the gas output from currently used anesthesia machines is taken up by the patient, and the remaining 95% is spilled into hospital scavenging systems or into the ambient environment of the operating room. Based on recent studies, concerns have arisen over the possible link between continued exposure to waste anesthetic gases and higher than average rates of spontaneous miscarriage, birth defects, and cancer among operating room personnel. Further, anesthetic gases collected by hospital scavenging systems are ultimately vented to the atmosphere. Nitrous oxide, which has an estimated medical use of 100,000 tons per year worldwide, has been found to deplete the atmosphere's ozone layer. Volatile anesthetics such as isoflurane, halothane and enflurane are chlorofluorocarbons which contribute to both ozone layer depletion and the greenhouse effect. The amount of chlorofluorocarbons released into the atmosphere from volatile anesthetics is estimated to be in excess of 2,000 tons per year. In addition to the environmental and health hazards of anesthetic release into the atmosphere, the economic loss can be substantial. Even assuming a high rate of anesthetic usage efficiency of about 50%, it is estimated that about $225,000,000 per year is wasted world wide on the loss of volatile anesthetics alone, excluding nitrous oxide and oxygen. This estimate may increase substantially if more expensive, improved volatile anesthetics like desflurane and sevoflurane become widely used.

In addition to the foregoing, commercially available anesthesia delivery systems have a number of operational limitations which detract from their usefulness and safety. In most widely used commercial designs, mechanical ventilation of the patient is possible only when the system is connected to a continuous supply of gas, e.g. from the hospital gas supply system. It is not possible to mechanically ventilate a patient with ambient, room air with these types of systems. Further, the ventilators of most anesthesia delivery systems cannot operate without a supply of compressed gas from cylinders or the like. As noted above, even though sensor arrays and electronic feedback loops have been incorporated to some degree in current anesthesia ventilator systems, the data acquired by such sensors often fail to accurately portray the actual parameters to be sensed, i.e. tidal volume, flow rate, pressure and the like. Incorrect or inaccurate measurements or data can have serious adverse effects, such as the gradual augmentation of the desired tidal volume supplied to the patient during mechanical inspiration.

SUMMARY OF THE INVENTION

It is therefore among the objectives of this invention to provide an apparatus operative as a ventilator and as an anesthesia delivery system, which reduces waste of anesthesia gases, which lowers net gas consumption, which provides for the effective delivery of a high fresh gas flow, which is operative in a variety of different modes of ventilation, which reduces escape of volatile anesthetics and nitrous oxide, which provides improved patient safety, which actively reduces the work of breathing on the part of a spontaneously breathing patient, which provides humidified air at the appropriate temperature, and, which provides improved user and real world interfaces.

These objectives are accomplished in a combination ventilation apparatus and anesthesia delivery system which comprises a circulation loop within which medical gases and oxygen, or a mixture of medical gases, oxygen and anesthetics, are circulated by a variable speed centrifugal blower to a Y-piece which connects the circulation loop to a face mask or to an endotracheal tube with which a patient can be intubated. A proportional flow control valve is operative essentially as a ventilator to actively control, in real time, the pressure at the Y-piece or carina or flowrate at the endotracheal tube in response to signals from pressure and/or flow sensors which are positioned to provide measurements truly representative of the actual pressure and flow conditions. Constant circuit volume is maintained by computer control of gas make-up valves in response to the movement of a weighted, hanging bellows located between the proportional flow control valve and the centrifugal blower inlet. Other elements of the system include an inline anesthetic vaporizer, a carbon dioxide absorber with or without a bypass, a bacterial filter, a heater/cooler assembly, a manual ventilation bag, flow rate and pressure sensors, a multigas analyzer, an exhalation purge valve and a scavenging system.

One aspect of this invention is predicated upon the concept of obtaining improved control over the pressure distribution within the system, the tidal volume or total quantity of air delivered to the patient during inhalation, and, the desired proportion of anesthesia gases and oxygen circulating within the circulation loop. This control is accomplished by obtaining data or measurements in real time at the appropriate locations within the circuit and/or endotracheal tube, and then processing such data in real time with effective controllers such as digital PID (Proportional, Integral, Derivative) control algorithms, to accurately control operation of the proportional flow control valve, purge valve, gas make-up valves and vaporizer which inject gases into the circulation loop. For example, in the presently preferred embodiment, flow is sampled at the distal tip of the Y-piece. The flow sensor is located between the Y-piece and the face mask, endotracheal tube or other airway device. A feed-back signal is provided from this flow sensor which is processed by a PID control algorithm to vary the size of the opening of the proportional flow control valve in order to ensure that the actually measured flowrate closely tracks the prescribed locus of flowrate over time, such that the desired tidal volume is actually delivered to the lungs within the given time allocated for inspiration. Because the pressure at any point in the loop is a function of (i) the size of the flow passage in the proportional flow control valve, (ii) the blower rotational speed and (iii) the volume of gas in the circuit or loop, modulation of the proportional flow control valve causes gas to be shunted into or out of the lungs depending upon the instantaneous pressure difference between the lungs and the Y-piece where the endotracheal tube, face mask, laryngeal mask airway or other airway device connects to the circulation loop.

Pressure is sampled at the distal tip of the endotracheal tube (when one is used) because it is a more accurate representation of the lung pressure, than, for example, pressure sampling at the Y-piece which suffers from such artifactual effects as the flow resistance of the endotracheal tube. This is particularly helpful when using the apparatus of this invention as a ventilator, e.g. in an intensive care unit, for assisting spontaneous inspiration and expiration. During assisted spontaneous inspiration, the proportional flow control valve closes down to direct flow to the patient's lungs, and, thus reduces the inspiratory effort that the patient's diaphragm must provide. During assisted spontaneous exhalation, the proportional flow control valve opens wider to suction flow out of the patient's lungs, assisting exhalation especially for patients with chronic obstructive pulmonary disease. The transition from spontaneous inspiration to exhalation is initiated by the patient and is detected by the change in flow direction measured by the flow meter located at the juncture of the Y-piece and airway device.

Computer control is also important to the efficiency with which anesthetic materials are added to the anesthetic circuit or loop. Oxygen and nitrous oxide are introduced into the breathing circuit during closed circuit anesthesia through gas make-up valves whose operation is controlled by the controller in response to signals from a microswitch and a linear optical encoder associated with the bellows on the suction side of the centrifugal blower. As gas is utilized by the patient during breathing, or because of loss from leaks, changes in the mass of gas within the circuit prevent the bellows from returning to its baseline position at the end of expiration. This, in turn, is monitored by the microswitch and linear encoder resulting in signals being sent to the controller. The controller, in turn, opens the make-up valves which allow additional oxygen and nitrous oxide to enter the circulation loop. The bellows also provides a collapsible volume from which gas can be transferred into the patient's lungs when the proportional flow control valve opening narrows down, e.g. during mechanical inspiration.

Other features of the system of this invention provide specific operational or safety advantages compared to commercially available ventilator and/or anesthesia delivery systems. A thermo-electric heater/cooler allows for both heating and cooling of the airway gases. In normal operation, the heater/cooler functions as a heater to maintain the temperature of the inspired gases at a desired set point and thus prevent heat loss from the patient. Additionally, operation of the centrifugal blower warms the gases within the circuit, at least to some extent. In emergency situations, however, such as in cases of malignant hyperthermia where the indicated therapy is to cool the patient, the thermo electric heater herein can be converted into a cooler by reversing the direction of flow of current therethrough. The cooled gases cool the patient. The patient, in turn, warms the cooled inspired gases to body temperature and humidifies them to the saturation point, thus cooling the patient.

This invention also includes a unique scavenging system which operates essentially independently of the vacuum source of the hospital in which the anesthesia delivery system is utilized. It has been found that fluctuations in the vacuum level from the central hospital source cause the vacuum within prior scavenging systems to also fluctuate. In this invention, a constant pressure vacuum is automatically maintained in the scavenging system manifold. No user adjustment is required, and the anesthesiologist is warned when gas is being spilled into the operating room. Further, a gauge or display on the front control panel of the anesthesia delivery system herein alerts the operator to the scavenging system manifold pressure and acts as a reminder that attention should be paid to the scavenging system during operation of the anesthesia delivery system.

Another aspect of this invention is predicated upon the concept of performing an oxygen flush of the circulation loop or breathing circuit without risk of barotrauma, or the creation of a flammable condition during laser surgery of the upper airway. From time to time, the anesthesiologist may desire to flush anesthetics and carbon dioxide from the circulation loop to reduce the concentration of same and/or to make up for loss of circuit gas volume. In past systems, an oxygen flush is initiated by the anesthesiologist by pressing a button with no safeguards to ensure that the anesthesia delivery system was properly configured for an oxygen flush, e.g. in the exhalation phase during mechanical ventilation, or whether the surgeon was operating a laser at the time. During an oxygen flush, a flow rate of about 60 l/m of oxygen is introduced into the breathing circuit which, in mechanical ventilation, can produce a risk of barotrauma if it occurs during mechanical inspiration. In the case of laser surgery of the upper airway, an oxygen flush increases the risk of flammable conditions within the upper airway should the laser accidentally puncture the endotracheal tube while a high concentration of oxygen is flowing therethrough.

In this invention, the oxygen flush is changed from a mechanically activated, independent event, to a controlled event. This control is obtained by splitting the oxygen flush event into an oxygen flush request module and an oxygen flush activate module. When the anesthesiologist presses the oxygen flush button, this amounts to a request for an oxygen flush which cannot be executed until hardware and software within the system configure the anesthesia delivery system so that the oxygen flush cannot harm the patient. That is, if the system was in the mechanical inspiration phase, the inspiration is aborted and the system configured for flushing. At the same time, the power to the laser employed by the surgeon is turned off to avoid potential harm to the patient. At this point, the oxygen flush is allowed to proceed.

Other improvements provided by this invention include an ability to ventilate a patient with room air in the event of loss of compressed gas by simply breaking the circulation loop between the blower inlet and the bellows. Further, a manual breathing bag is connected to the circulation loop and remains therein regardless of the mode of ventilation to provide the anesthesiologist with the ability to manually ventilate the patient at all times and to physically feel the compliance of the patient's lungs, as well as any spontaneous breaths, by grasping the bag during ventilation.

DESCRIPTION OF THE DRAWINGS

The structure, operation and advantages of the presently preferred embodiment of this invention will become further apparent upon consideration of the following description, taken in conjunction with the accompanying drawings, wherein:

FIG. 3 is a schematic view of the heater/cooler employed in the anesthesia circuit or loop;

FIG. 4 is a cross-sectional view taken generally along line 4—4 of FIG. 3;

DETAILED DESCRIPTION OF THE INVENTION

Figure 1:
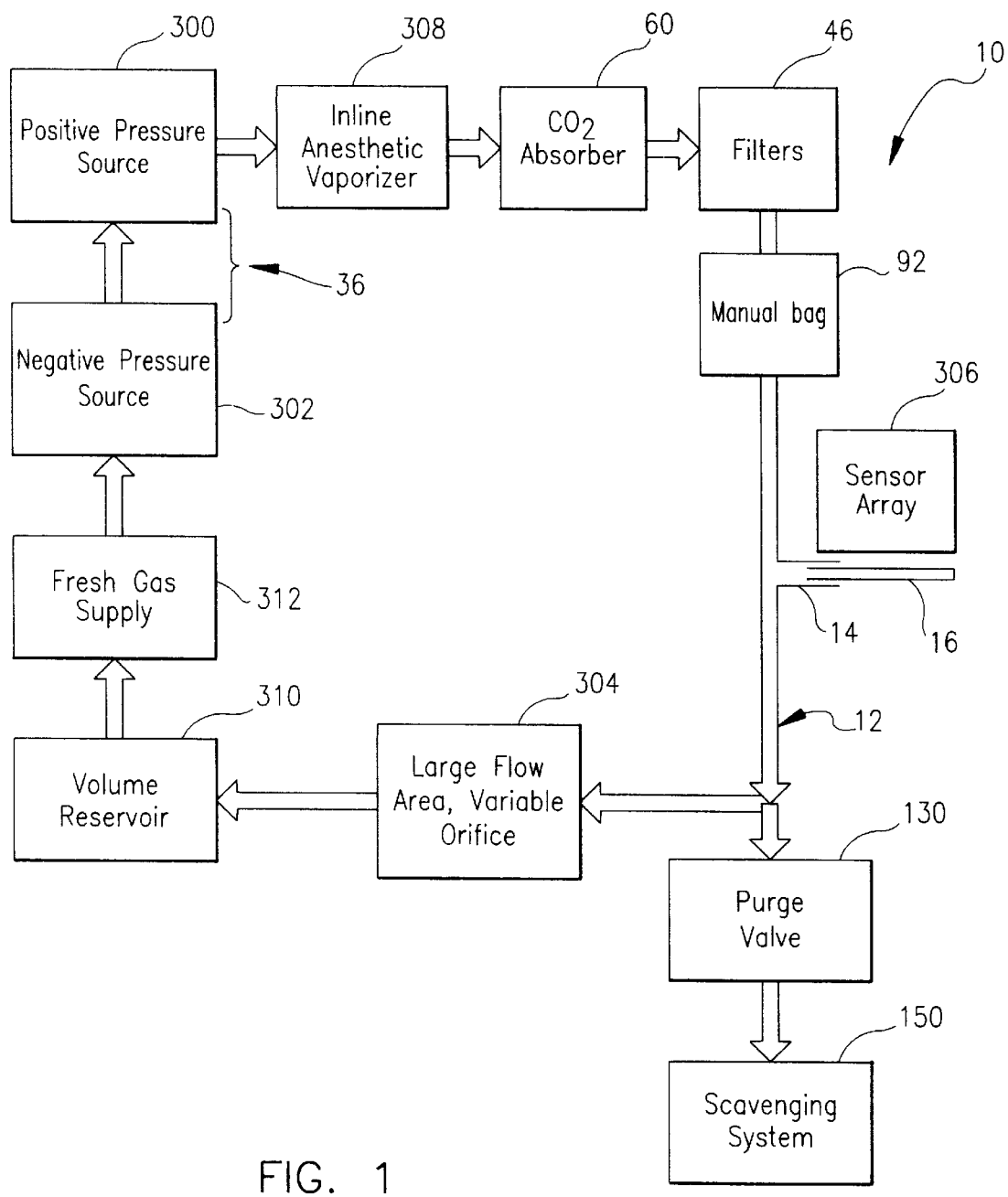
FIG. 1 is a schematic view of the blower recirculated, ventilation and anesthesia delivery system of this invention.

Referring initially to FIG. 1, the ventilation and anesthesia delivery system 10 of this invention is schematically illustrated. As mentioned above, the system 10 of this invention can be utilized solely as a ventilator, e.g. in intensive care units, even with patients having lungs of relatively low compliance. The system 10 is also effective as an anesthesia delivery system for patients in the operating room under general anesthesia. For purposes of the present discussion, the system 10 will most often be referred to in the mode of operation wherein anesthesia gases are delivered to a patient, but it should be understood that such discussion is in no way limiting of the scope of this invention and that the system 10 can be readily employed as a ventilator.

Figure 1A:
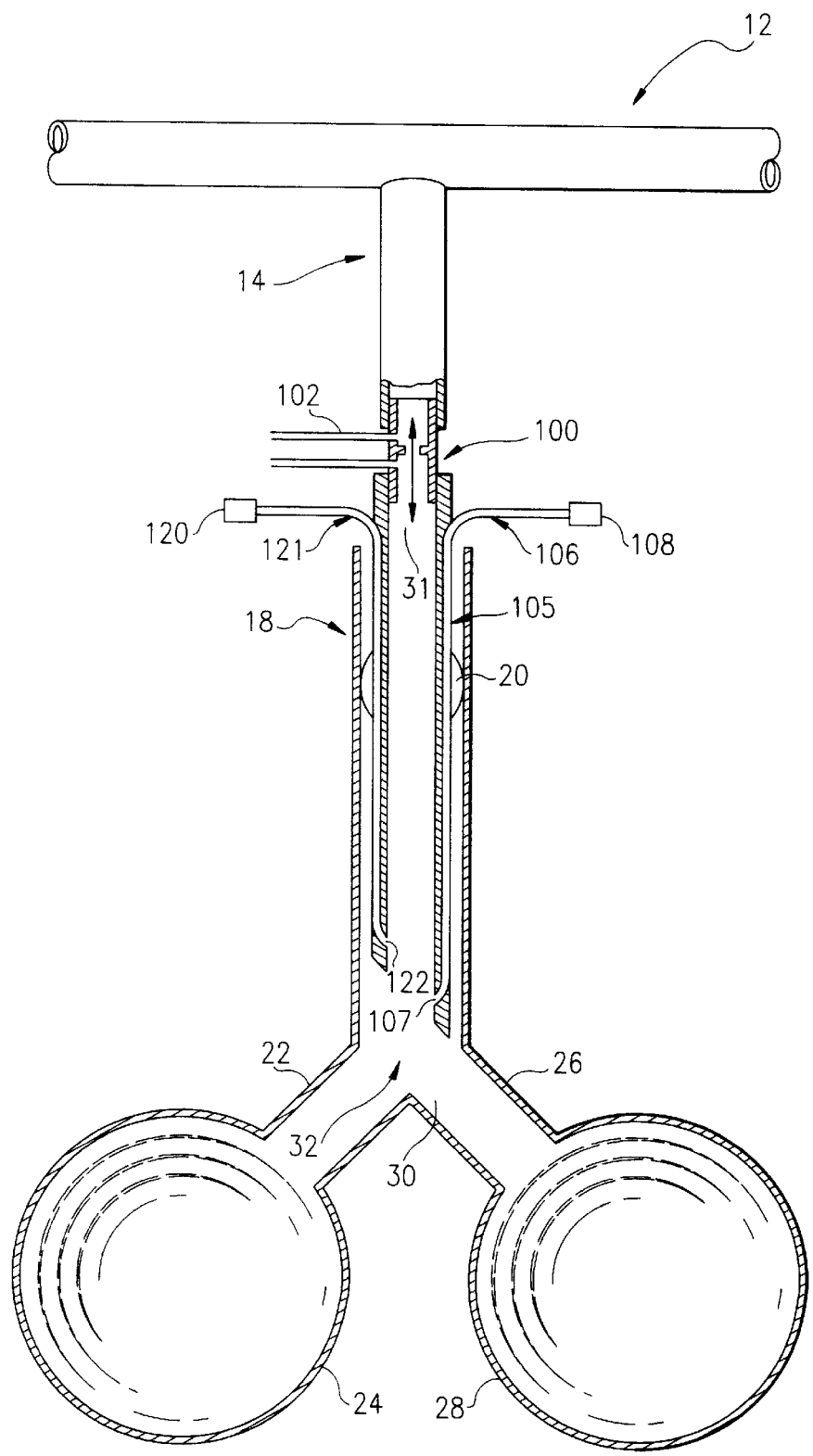
FIG. 1A is an enlarged view of the endotracheal tube, Y-piece and the patient's airways.

Generally, the ventilator and anesthesia delivery system 10 comprises an anesthesia circuit or circulation loop 12 in which a number of individual system elements, described below, are interconnected by lengths of corrugated hose. In one embodiment, the circulation loop 12 is connected by a Y-piece 14 (also known as a "T-piece") to an endotracheal tube 16 which is inserted within the trachea 18 of a patient, as schematically depicted in FIG. 1A. A cuff 20 is provided on the exterior surface of the endotracheal tube 16 which is inflated to create a seal with the trachea 18. It should be noted that other airway devices such as a face mask could be employed instead of the endotracheal tube 16. For purposes of the present discussion, the left bronchus 22 and left lung 24 are referred to as one respiratory passageway, and the right bronchus 26 and right lung 28 form the second respiratory passageway. The bronchi 22, 26 meet at the carina 30 where the distal tip 32 of the endotracheal tube 16 is positioned.

Overall System Construction and Operation

Before describing the elements of one presently preferred embodiment of system 10 in detail, it is believed to be helpful to consider the overall scheme of operation of system 10 as depicted in block diagram form in FIG. 1. The system design can be perhaps more easily understood from an operational or functional point of view, without initial reference to the particular elements employed in the presently preferred embodiment.

The circulation loop 12 provides a path for the circulation of gases to and from a patient. Such circulation is achieved by operation of a centrifugal blower 36 having an outlet which functions as a positive pressure source and an inlet operative as a negative pressure source. These positive and negative pressure sources are depicted schematically in FIG. 1 as blocks 300 and 302, respectively, and are collectively labeled with the reference 36 to designate the blower 36. The blower 36 may be either a fixed speed or variable speed type device. At any time, the maximum pressure in the circuit 12 is at the outlet of the blower 36, while the minimum pressure (sub-atmospheric) in the circuit 12 is at the blower inlet. A variable flow orifice, located in the circuit 12 between the Y-piece 14 and inlet of blower 36, acts as a variable flow resistance in the recirculating flow path. This variable flow orifice is designated by block 304 and is identified as a large flow area variable orifice, which refers to the functional operation of such valve. If the variable flow orifice is operated to increase resistance to flow (e.g. partially closed) the pressure at the Y-piece moves closer to the blower outlet pressure, while if the flow resistance is decreased, the pressure at the Y-piece moves closer to the subatmospheric pressure at the blower inlet. In turn, the pressure at the Y-piece 14 relative to the pressure in the lungs 24, 28 determines whether gas flows into or out of the lungs 24, 28. Consequently, the variable flow orifice provides a means of moving gas in and out of the lungs 24, 28.

Operation of the variable flow orifice is controlled in response to signals generated by a sensor array identified by block 306 in FIG. 1, which includes a flow/pressure monitor at the Y-piece 14 and a pressure sensor at the distal tip 32 of the endotracheal tube 16. See also FIG. 1A. The variable flow orifice is controlled under flowrate feedback when it is controlling the flowrate during inspiration, i.e. active inflation and inspiratory pause. During manual ventilation in a closed circuit, the variable flow orifice acts as an adjustable pressure limiting valve providing a controlled leak therepast and back into the recirculating flow.

Anesthetic agent is introduced into the circuit 12 by an inline anesthetic vaporizer, labelled block 308 in FIG. 1, which preferably includes a motorized syringe pump described in detail below. Liquid anesthetic is injected into the high recirculating gas flow within the circuit 12 and is effectively vaporized before it reaches the patient's lungs. The control of the inspired agent concentration is independent of the gas composition control.

A carbon dioxide absorbent canister 60, located in the circulation loop 12, absorbs the carbon dioxide exhaled by the patient so that exhaled gases can be re-used. The gas within the circuit is filtered by a bacterial filter 46 leading to a manual breathing bag 92 which remains in the breathing circuit 12 at all times. The manual bag 92 has been modified from ordinary bags of this type, by making it very stiff to expansion while remaining compliant to collapse e.g. during a spontaneous breath or manual squeezing. This unidirectional increase in stiffness of the bag 92 avoids making the circuit compliance too large such that tidal volume would have been diverted into the bag 92 instead of to the patient.

The block labelled 130 in FIG. 1 designates a purge valve which leads to a scavenging system 150. The purge valve 130 allows gas to be expelled from the circuit 12 to the scavenging system 150 when a large change in inspired agent or gas concentration is requested. The purge valve 130 also acts as adjustable pressure limiting valve when the system is running in open circuit, e.g. during pre-oxygenation.

The block 310 labelled "Volume Reservoir" refers to a weighted bellows which acts as a capacitor or buffer for storing gas exhaled from the lungs and returning it back to the lungs during inflation. The weights are required to counteract the sub-ambient pressure at the bellows due to its proximity in the circuit 12 to the inlet of the blower 36. A linear encoder attached to the bellows allows software within the system controller, described below, to determine how full the bellows are at any given time. In the presence of a leak, the bellows collapse and provide a visual indication to the user just like in a bellows which descends during inspiration in other anesthesia systems. In the absence of a leak and without consumption from the patient, and without an influx of fresh gas into the system and at constant blower speed, the bellows always returns to the same or baseline position at end exhalation, during closed circuit operation. This feature or characteristic of the bellows is utilized to control the volume of gas within the circuit 12 during closed circuit operation. If the bellows does not return to its baseline position at end exhalation, then gas is added to the system via the fresh gas supply labelled block 312 in FIG. 1, which, as described below, are fresh gas feed valves. Such gases are added at a total flow rate which is proportional to the distance of the bellows at end exhalation from the baseline position, until eventually the bellows returns at end exhalation to its baseline position. The circuit volume control thus enables the oxygen consumption rate or leak rate to be quantified during closed circuit operation. The baseline position for the bellows is offset from the mechanical base of the bellows, which incorporates a microswitch. The microswitch is used to reinitialize the linear encoder whenever the bellows "bottoms out" and touches its mechanical base, thus triggering the microswitch.

Description of Preferred Embodiment

Each of the individual elements of one presently preferred embodiment of the system 10 is described separately below, followed by a discussion of the overall operation of system 10 including certain particular operational sequences which are of interest. For ease of reference, the system elements are described beginning with the data acquisition and control system or controller 34, followed by a description of each system element within circulation loop 12 starting with the centrifugal blower 36. The discussion proceeds in a clockwise direction around the loop 12 from blower 36, in the same direction as the flow of gas therethrough as depicted by the arrows 37.

Data Acquisition and Control System—Controller

Figure 2:
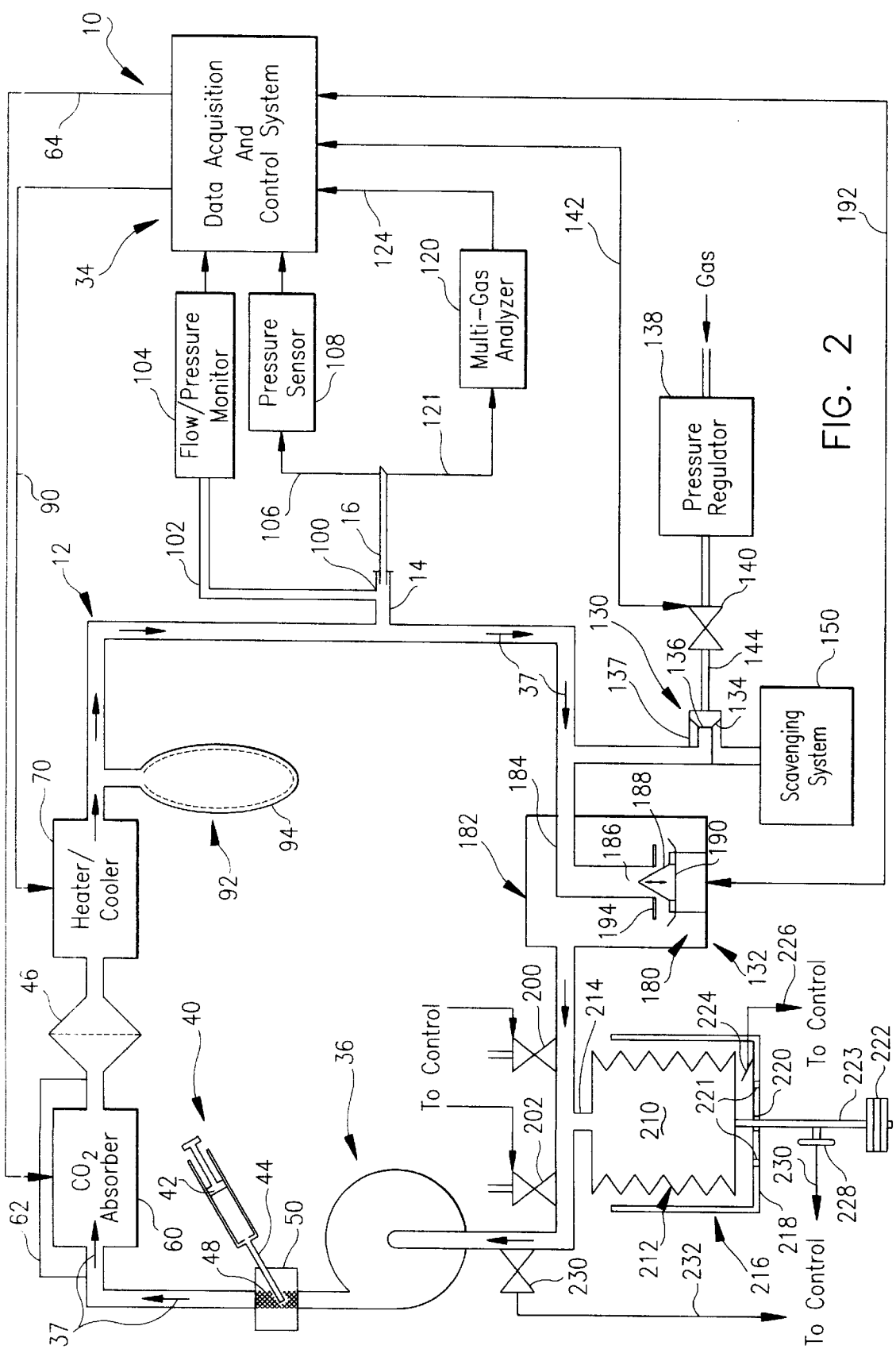
FIG. 2 is a view of one presently preferred embodiment of the system shown in FIG. 1.

As schematically depicted in FIG. 2, the data acquisition and control system or controller 34 of this invention is based on a 80486/66 CPU, with added A/D and D/A data acquisition cards. The detailed construction of the controller 34 forms no part of this invention of itself, and is therefore not described herein except insofar as the operation of controller 34 interfaces with various other system elements, as described below. The controller 34 controls all aspects of the system function, particularly in the mechanical ventilation mode of operation, and provides a number of safety features which are not present in prior designs. The design and reduction to practice of the system 10 of this invention was achieved with the operational capabilities of controller 34 as an integral part of the system 10 to maximize its capabilities and benefits.

Centrifugal Blower

The blower 36 is a variable speed centrifugal blower of the type preferably manufactured by Ametek, Lamb Electric Division, under Model No. 116639-2-E. The blower 36 has backward curved blades which provide a monotonic or non-pulsing discharge curve, and, therefore, stable operation without surges. The blower 36 has the characteristic that the maximum ("shut-off") pressure that can be generated at the blower outlet is a function of the rotational speed of the blower 36. This shut-off pressure feature is employed as a safety measure wherein the default blower speed is set so that the maximum pressure that can be generated within the circuit 12 is 20 cm $H_2O$ or some other default pressure value. Nevertheless, the blower default setting can be manually overridden, as desired, to deliver a pressure of up to 150 cm $H_2O$ so that patients having lungs with "stiff" or low compliance can be ventilated. The mechanical work generated by the blower 36 also heats the recirculated gases, which is a desirable side effect.

Injection of Volatile Anesthetics

As noted above, normal inhalation anesthetics for surgery include an intermixture of oxygen, nitrous oxide and a volatile anesthetic such as halothane. In the presently preferred embodiment, an unvaporized liquid volatile anesthetic is introduced into the circulation loop 12 by a computer controlled, motorized syringe pump 40 having a plunger 42, in response to a signal from the controller 34. See FIG. 2. One syringe pump 40 suitable for this purpose is a Harvard Apparatus Pump 22 available from Harvard Apparatus, Inc. of South Natick, Mass. In order to prevent liquid anesthetic from reaching the patient's lungs 24, 28, the syringe pump 40 is located within the loop 12 as far away from the Y-piece 14 as possible. This increases the likelihood that all liquid anesthetic drops are vaporized by the time they reach the patient's respiratory system.

Preferably, the syringe pump 40 is provided with a very high flow resistance, narrow bore (20 gauge, 0.024 inch i.d.) needle 44 to create a large back pressure within the syringe pump 40 which prevents spontaneous vaporization. The narrow bore of the needle 42 also presents a lower area for vaporization of the liquid anesthetic at the needle tip. Uncontrolled vaporization is further reduced by locating the needle 44 at the exhaust side of the blower 36 which is the site of highest pressure within the circulation loop 12. Additionally, a bacterial filter 46 is located within the loop 12 downstream from the liquid anesthetic injection site and upstream from the patient. In the highly unlikely event of incomplete vaporization, liquid anesthetic drops larger than the pore size of the bacterial filter 46 are trapped on the filter material and eventually vaporize.

The needle 44 of syringe pump 40 delivers the liquid anesthetic into a sintered metal insert 48 carried within a copper block 50 mounted in the circuit 12. Due to the low thermal inertia of the plastic tubing or corrugated hose interconnecting the circuit elements, there may be a chance of "pooling" of the liquid anesthetic within the circuit 12 with the subsequent risk of anesthetic being delivered in liquid form to the lungs. This potential problem is avoided by the large thermal inertia of the copper block 50 and the large surface area and wicking action of the sintered metal insert 48 into which the liquid anesthetic is injected. Such elements 48, 50 ensure complete vaporization of the liquid anesthetic even at high injection rates of up to 10 ml/min. of liquid halothane.

Preferably, the syringe pump 40 is located at a lower elevation than the point in the circulation loop 12 where the liquid anesthetic is introduced. This anesthetic introduction point, in turn, is lower in elevation than the Y-piece 14 and the endotracheal tube 16 to prevent the possibility of gravity feed of liquid anesthetic into the patient's lung 24, 28 in the event of catastrophic failure of the system. The syringe pump 40 should also be positioned such that the needle end of the syringe is always lower than the plunger end thereof. This ensures that any air in the syringe floats to the top against the face of plunger 42.

$CO_2$ Absorber

A $CO_2$ absorber 60 is located within the circulation loop 12 downstream from the syringe pump 40. In the presently preferred embodiment, the $CO_2$ absorber 60 is fabricated from a length of transparent plastic pipe having end caps affixed on either end, one of which is provided with a threaded end piece to permit emptying and refilling of a $CO_2$ cartridge (not shown) within the interior thereof. Preferably, steel mesh screens are located on the inside of each end piece of the plastic pipe to prevent carbon dioxide absorbent dust or granules from being blown into the circulation loop 12.

In cases where it is desired to wash away volatile anesthetics rapidly from the loop 12, a bypass line 62 is activated by controller 34 via a control line 64 to direct the flow of gases within the loop 12 around the $CO_2$ absorber 60. This allows the patient to be hyperventilated without excessively lowering alveolar $CO_2$ concentrations to assist in removal of the volatile anesthetics.

Heater/Cooler

One benefit of closed circuit anesthesia systems of the type disclosed in this invention is that humidity and heat are better conserved compared to open anesthesia circuits wherein gases exhaled by the patient are not recirculated. Nevertheless, a heat loss of the gases is experienced in the course of their contact with the tubing and other elements within circulation loop 12 because they are at ambient temperature, e.g. about 25° C., compared to the temperature within the patient's lungs of about 38° C. Cooling of circuit gases from 38° C. to 25° C. leads to condensation, and, in turn, the gases returning to the patient within the closed circulation loop 12 carry less water than exhaled gases. In restoring the relative humidity of the exhaled gases back to 100% at 38° C., the patient's respiratory system has to supply the latent heat of vaporization of water, resulting in undesirable cooling of the patient.

With reference to FIGS. 3 and 4, a heater/cooler 70 is schematically depicted which is positioned in the circulation loop 12 downstream from the bacterial filter 46. The heater/cooler 70 is formed of a core of intersecting copper fins 72 carried within a housing 74, thus forming a flow passage for gases having an inlet 76 and an outlet 78. A water trap 80 is connected at the base of the housing 74 which is provided with a drain plug 82.

The heating power for the heater/cooler 70 is preferably provided by a number of thermo-electric, Peltier modules 84 mounted at intervals about the circumference of the housing 74. Peltier modules 84 have the property that if the direction of current flow therethrough is changed, then the heating side of the module 84 becomes the cooling side and vice versa. Temperature along the copper fins 72 is preferably measured by at least two thermistors 86, 88, one located toward the exterior portion of the copper fins 72 and the other near the interior.

In normal operation, the Peltier modules 84 of heater/cooler 70 are energized to heat the copper fins 72 and, in turn, warm the gases passing therethrough and entering the patient's lungs to a level of about 38° C. Nevertheless, the bidirectional heat transfer capability of the Peltier modules 84 is useful for active cooling of the breathing circuit gases for the treatment of patients during malignant hyperthermia, wherein the indicated treatment therapy is to cool the patient. Cooled air introduced into the patient's lungs contacts the large surface area thereof to transfer heat from the lungs, and the resulting latent heat of condensation effectively lowers the core temperature of the patient. When used as a cooling device, the water trap 80 is used to collect and remove water which condenses within the interior of heater/cooler 70.

As schematically depicted in FIG. 2, the heater/cooler 70 is connected by a line 90 to the controller 34. The thermistors 86, 88 each send a signal to the controller 34 indicative of the temperature within heater/cooler 70. Because the thermistors 86, 88 are located at different positions within heater/cooler 70, their weighted average is calculated by the controller 34 to obtain the mean temperature within heater/cooler 70. A feedback loop is provided within controller 34 to alter the temperature of the copper fins 74 via adjustment of current flow to the Peltier modules 84, so that the temperature of the breathing circuit gases can be maintained within acceptable limits.

Manual Breathing Bag

In the presently preferred embodiment, a manual breathing bag 92 is connected to the recirculation loop 12 downstream from the heater/cooler 70. The presence of the breathing bag 92 allows the anesthesiologist to ventilate the patient's lungs manually by periodically squeezing the bag 92, and also to obtain a tactile feel for the compliance and resistance of the patient's respiratory system. Collapse of the bag 92 when the patient takes spontaneous breaths as the anesthetic wears off and the patient starts waking up also helps the anesthesiologist to detect inadvertent light anesthesia or confirms the onset of emergence from anesthesia. The breathing bag 92 also acts as a buffer and collapses to provide gas flow to a spontaneously breathing patient if the spontaneous inspiratory flow rate demand exceeds the flow rate in the circulation loop 12, thus helping to reduce the work of breathing on the part of the patient.

One potential problem with manual breathing bags contained in prior systems is that during mechanical ventilation, they divert part of the set tidal volume away from the patient because of the compliance thereof. As a result, prior ventilators and anesthesia systems have locked out or isolated the manual bag from the breathing circuit during mechanical ventilation. This requires affirmative steps on the part of the anesthesiologist to effect the changeover from manual to mechanical ventilation.

In order to avoid isolating the manual bag 92 from the circulation loop 12 of this invention, the manual bag 92 is preferably provided with a mesh of fine, high tensile strength nylon 94 or other suitable material such as heavy duty packing tape which is affixed onto the outside surface of its rubber sidewall. See schematic depiction in FIG. 2. This design of manual bag 92 is intended to allow the bag 92 to fully deflate upon inhalation of the patient, but limit the compliance or inflation of the bag 92 to a predetermined, maximum shape. The nylon mesh 94 or packing tape functions to restrict the elasticity of the bag 92 in an expanded condition, so that the manual bag 92 becomes very stiff past a fixed, fully inflated volume and therefore does not interfere or divert away an inordinate part of the mechanical tidal volume intended for the patient.

Flow Meter

With reference to FIGS. 1A and 2, a flow sensor 100 is mounted at the proximal end 31 of the endotracheal tube 16, and is connected by lines 102 to a flow/pressure monitor 104. The purpose of the flow sensor 100 is to measure the flow rate of gas into the lungs 24, 28 for feedback control of inspiratory flow rate during mechanical ventilation, and, to measure the direction of flow of air within the endotracheal tube 16 or other airway device. The flow sensor 100 is positioned at the proximal end 31 of endotracheal tube 16 because at that location flow rate measurements can be integrated over time to represent the true tidal volume supplied to the lungs. Additionally, location of the flow sensor 100 at the proximal end 31 of endotracheal tube 16 permits measurement of exhaled volume as a safety measure, i.e. if the exhaled volume is significantly smaller than the inspired volume a leak is present downstream from the flow sensor 100, such as at the cuff 20 which seals the endotracheal tube 16 within the trachea 18. One type of flow sensor 100 suitable for use in the system 10, is an obstructive flowmeter with a differential pressure transducer commercially available under the name "Novametrix FloTrak" from Novametrix Medical Systems, Inc. of Wallingford, Conn.

As discussed in detail below in connection with a discussion of the operation of system 10, feedback loops are employed within the controller 34 to adjust the flowrate of gas through the endotracheal tube 16 in response to signals from the flow sensor 100. Further, the signals representative of the direction of flow within the endotracheal tube 16 are utilized to identify respiration and expiration, and where they precisely start.

Pressure Sampling and Pressure Transducers

Airway pressure is sampled at the distal tip 32 of the endotracheal tube 16 by a lumen 105 embedded in the wall of the endotracheal tube 16 having a sampling port 107. A line 106 extends from the lumen 105 to a pressure sensor or transducer 108, preferably of the type sold under Model No. 163SC01D48 by SenSym, Inc. of Milpitas, Calif. In addition to the pressure transducer 108, a second pressure transducer within the sensor 100 is mounted to the Y-piece 14 as a design safety feature in the event that the pressure sampling port at the distal tip 32 of endotracheal tube 16 becomes occluded.

There are several reasons for measuring pressure at the distal tip 32 of endotracheal tube 16. One important factor is that the pressure at the distal tip 32 is a much more accurate representation of the actual pressure within the lungs 24, 28 than any other location within the circulation loop 12. The flow resistance of the endotracheal tube 16 itself is orders of magnitude higher than that of the remainder of the circulation loop 12 thus causing pressure readings at the Y-piece 14 or at carbon dioxide absorber 60, for example, to be higher and lower than actual lung pressure particularly during spontaneous inspiration and expiration, respectively. This becomes a significant factor when using the system 10 as a ventilator to assist spontaneous breathing with the objective of reducing the work of breathing on the part of the patient.

Gas Sampling

As schematically depicted in FIGS. 1A and 2, a multi-gas analyzer 120, preferably of the type sold by Datex of Finland, is connected by a line 121 to a sampling port 122 located at the distal tip 32 of endotracheal tube 16. The sampling port 122 is placed at that location, because if gas concentrations were monitored at the Y-piece 14, for example, or any other location around the circulation loop 12, measurements would be diluted by the recirculating flow of fresh gases. The multi-gas analyzer 120 is capable of measuring concentrations of carbon dioxide, oxygen, nitrous oxide and volatile anesthetics, and produces signals representative of such concentrations which are sent to the controller 34 via line 124, as schematically depicted in FIG. 1. As discussed more fully below, in response to real time measurements of the gas concentrations at the distal tip 32 of endotracheal 16, control software within controller 34 is operative to control the introduction of volatile anesthetics, oxygen and nitrous oxide into the circulation loop 12 in relative proportions sufficient to maintain the desired concentrations of same for supply to the patient.

Exhalation or Purge Valve

As depicted in FIGS. 1 and 2, an exhalation or purge valve 130 is connected to the circulation loop 12 at a location downstream from the Y-piece 14 and upstream from the proportional flow control valve 132 described in detail below. The purge valve 130 is preferably a mushroom valve of the type sold by Inspiron of Rancho Cucamonga, Calif., having a mushroom-shaped rubber diaphragm 134 which is movable between a closed position against the opening 136 of a tube 137 connected to loop 12 as depicted in FIG. 2, and an open position spaced from such opening 136. The purge valve 130 is pressurized, e.g. so that its rubber diaphragm 134 engages or closes against opening 136, with compressed air which is regulated down to a pressure of 100 cm $H_2O$ by a miniature precision pressure regulator 138 of the type sold by Airlogic of Racine, Wis., under Model No. R100. The supply of pressurized air to the purge valve 130 is controlled by a three-way NC pilot valve 140 of the type sold by Clippard Laboratories, Inc. of Cincinnati, Ohio, under Model No. EV-3, in response to signals received from the controller 34 via line 142. The charging air which closes the purge valve 130 is discharged through the exhaust port (not shown) of the pilot valve 140 when it is de-energized.

Preferably, the pilot valve 140 and purge valve 130 are interconnected by a length of tubing 144 having a relatively large internal diameter but short length to obtain rapid depressurization of the purge valve 130 when the pilot valve 140 is de-energized.

In the closed circulation loop 12 of this invention, the presence of purge valve 130 is necessary for a number of reasons. For example, during an oxygen flush described below, oxygen is introduced into the circulation loop 12 at a flow rate on the order of 60 l/min. Undesirably high pressures are obtained in a short period of time within loop 12 without opening the purge valve 130 to provide a path to discharge the gas mixture within the loop 12, and the purging oxygen, to an external scavenging system 150 described below. The purge valve 130 is also useful to effect rapid changes in the concentration of gases within circulation loop 12 by providing a path for their escape, if desired. Additionally, the purge valve 130 provides a safety factor in the event of a malfunction in the proportional flow control valve 132, e.g. in situations where the valve 132 would improperly remain in the closed position and thus create a rapid build up of pressure within the loop 12.

Scavenging System

Figure 5:
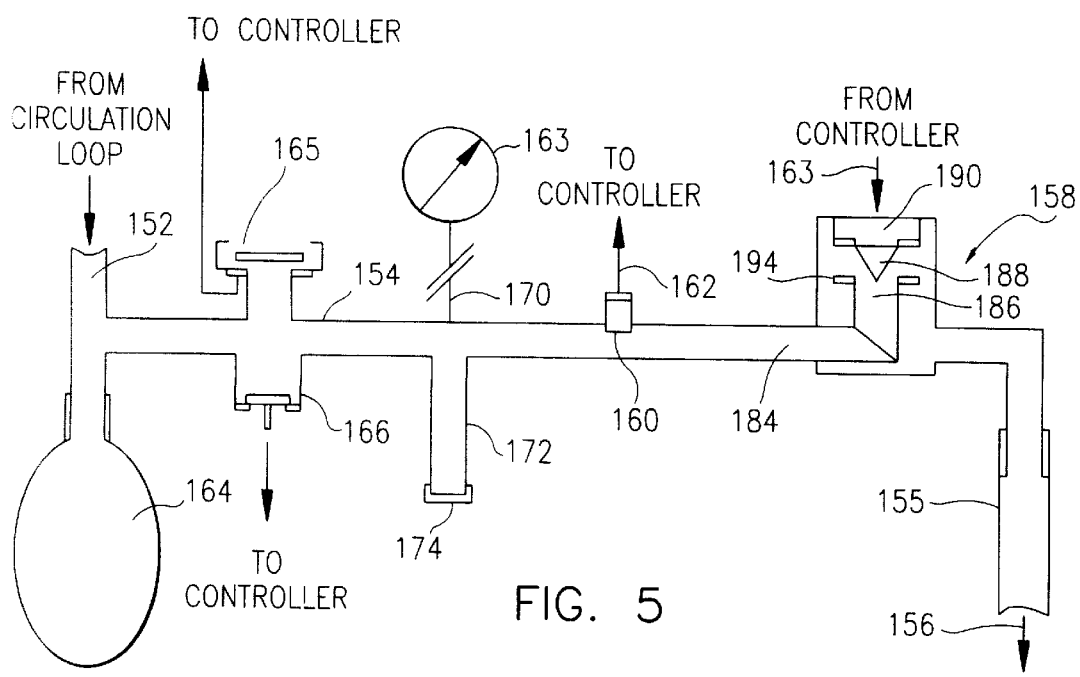
FIG. 5 is a schematic view of the scavenging system of this invention.

With reference to FIGS. 2 and 5, the scavenging system 150 of this invention is connected to the outlet of the purge valve 130 to receive gases discharged from the circulation loop 12 of system 10. As noted above, scavenging systems employed in other anesthesia delivery systems are essentially completely dependent upon the central vacuum source of the hospital in which the equipment is utilized and the fixed adjustment of a needle valve in the scavenging system manifold. In the event of large fluctuations in the vacuum of such central vacuum systems, an unpredictable negative pressure may be exerted on the anesthesia circuit to which they are attached.

The scavenging system 150 of this invention avoids such fluctuations in vacuum by providing a construction which operates essentially completely independently of the central vacuum system of a hospital or the like. As shown in FIG. 5, the scavenging system 150 is connected by a hose 152 to the circulation loop 12 which, in turn, connects to one end of a manifold 154. The opposite end of manifold 154 is joined by a tube 155 to the hospital central vacuum depicted schematically by arrow 156 in FIG. 5.

In the presently preferred embodiment, substantially constant vacuum is maintained within the manifold 154 by a proportional flow control valve 158 which is essentially identical to valve 132, described in more detail below. The same reference numbers used to describe valve 132 below are included in FIG. 5 to depict the same structure within valve 158. To achieve control of the vacuum within manifold 154, the vacuum level within scavenging manifold 154 is sensed by a pressure transducer 160, located upstream from the proportional flow control valve 158. The pressure transducer 160 sends a signal via line 162 to the controller 34, which, in turn, produces a control signal through line 163 to open and close valve 158, as required, in order to maintain substantially constant pressure or vacuum within scavenging manifold 154. The proportional flow control valve 158 therefore acts as a back pressure regulator within manifold 154 so that the upstream portion of the scavenging system 150, including connecting hoses 152, is exposed to a substantially constant pressure or vacuum irrespective of fluctuation in the central vacuum level at 156. Preferably, a bag 164 is connected to the upstream end of manifold 154 to buffer any sudden large flow rates of gas entering the scavenging system 150 from loop 12.

The scavenging system 150 also includes structure for sensing an overload or malfunction therein during operation. With reference again to FIG. 5, a gravity pressure relief valve 165 and a gravity vacuum relief valve 166 are connected to the manifold 154, opposite one another, and downstream from the connector hose 152. Additionally, a pressure/vacuum gauge 168 located on the display panel of system 10 (not shown) is connected by a line 170 to the manifold 154. In the event pressure within the scavenging system 150 varies either above or below ambient by more than a predetermined level, e.g. 10 cm $H_2O$, such variation is detected by the transducer 160 which sends a signal to controller 34. Additionally, signals are sent from the relief valves 165 or 166 to the controller 34 indicative of a high or low pressure condition within the scavenging manifold 154. For example, if an increase in pressure within the manifold 154 occurred, valve 165 is opened. On the other hand, in the event of a decrease in pressure below ambient within the manifold 154, the valve 166 is opened. Preferably, the controller 34 is programmed to activate an alarm (not shown) if either of the relief valves 165 or 166 remains open after a predetermined period of time. This alarm signifies that gas, usually containing anesthetic, is either being spilled into the operating room (with valve 165 open), or excessive vacuum is present in the scavenging manifold 154 (with valve 166 open).

In the event no central vacuum system is available, the scavenging system 150 is operated as a passive rather than active system. This is achieved by connecting one end of a passive scavenging tube 172 to a window or a non-recirculating air-conditioning system exhaust grille via a hose (not shown). The opposite end of tube 172 is connected to manifold 154, as shown. For purposes of illustration, the tube 172 is shown with a cap 174 which is utilized when the hospital vacuum system is available.

Proportional Flow Control Valve

With reference to FIG. 2, the proportional flow control valve 132 is interposed within the circulation loop 12 downstream from the endotracheal tube 16 and upstream from the suction side of blower 36. The proportional flow control valve 158 employed in the scavenging system 150 is essentially identical to valve 132, as noted above, and is therefore not described separately herein.

Because of the potentially high flow rates through the circulation loop 12, and the need to maximize the range of flow available, the proportional flow control valve 132 is designed with a large flow orifice, e.g. on the order of 2.54 cm in diameter, and a flow resistance of less than 1 cm $H_2O$ pressure drop at 60 l/min flow. These design specifications were obtained using a woofer speaker 180 as a proportional, linear motion actuator. The woofer speaker 180 is commercially available from MTX Oaktron of Monroe, Wis. under part Nos. 16W312, SH0063-51, 6MCO22 and SHF021. The woofer speaker 180 is preferably encased in an airtight, transparent enclosure 182 made of plexiglass or other suitable rigid material. The enclosure 182 receives a tube 184 having an inlet end connected to the circulation loop 12 and a discharge end 186 positioned immediately adjacent the profiled plug 188 of the woofer speaker 180 which is mounted atop the woofer diaphragm 190. Preferably, the profiled plug 188 is fabricated from Delrin or a similar material and has an outer wall which increases in diameter from the tip thereof to a base having a diameter at least equal to the diameter of the discharge end 186 of tube 184. The woofer speaker 180 is driven by a signal transmitted via line 192 from controller 34 which causes the profiled plug 188 to move toward and away from the discharge end 186 of inlet tube 184 along a distance on the order of about 9 to 11 mm. As depicted in FIG. 2, the inlet tube 184 and profiled plug 188 are positioned with respect to one another so that full extension of the profiled plug 188 by woofer diaphragm 190 causes the profiled plug 188 to contact the discharge end 186 of inlet tube 184 and thus close the flow of gas therethrough. In order to obtain a seal therebetween, a flat doughnut 194, formed of foam rubber or the like, is mounted to the woofer diaphragm 190 in a position to engage the discharge end 186 of inlet tube 184.

The operation of proportional flow control valve 132 is described in detail below. It has a number of uses, and provides the system 10 with substantial versatility of operation, both as a ventilator and an anesthesia delivery device.

Gas Make-up Valves and Oxygen Flush

As mentioned above in connection with a discussion of the motor-operated syringe pump 40, oxygen and nitrous oxide or another type of medical gas are selectively introduced into the circulation loop 12 during operation of the system 10 as gas is used by the patient or as it leaks out of the system 10, either accidentally or intentionally. With reference to FIG. 2, this function is provided by gas make-up valves 200 and 202 which are connected to circulation loop 12 downstream from the proportional flow control valve 132. Make-up valve 200 is connected to a supply of oxygen described below in connection with a discussion of FIG. 6, and make-up valve 202 is connected to a source of nitrous oxide (not shown) another anesthetic gas or essentially any other clinical gas such as nitrogen, helium and the like. Preferably, gas make-up valves 200, 202 are proportional flow control valves of the type sold by LDI Pneutronics Corp. of Hollis, N.H., under Model No. VSO, 525 body. Valves 200, 202 are mounted directly onto standard 15 mm ID connectors (not shown) which, in turn, are connected to the circulation loop 12. Mounting of valves 200, 202 to standard connectors minimizes the residual volume of gas between valves 200, 202 and the loop 12.

In addition to providing make-up oxygen to the circulation loop 12, the make-up valve 200 can be operated to perform an $O_2$ flush of the circuit 12, as desired by the clinician. The purpose of an $O_2$ flush is to (1) compensate for a large leak in the system 10, (2) quickly flush away or wash out anesthetics from the circulation loop 12, and (3) rapidly change the concentration of inspired oxygen within the loop 12. As noted above, two concerns arise with patients' safety in connection with the performance of an $O_2$ flush. The patient's lungs must be protected against overinflation or barotrauma when the relatively high flow of pure oxygen, e.g. 60 l/min, is introduced into the circulation loop 12. Secondly, when performing laser surgery on the upper airway, an inadvertent puncture of the endotracheal tube 16 by the laser while an $O_2$ flush is underway could result in an airway fire. Accordingly, the system 10 of this invention is configured to perform an $O_2$ flush in a two-step process, including a request for an $O_2$ flush and proper configuration of the circulation loop 12, followed by actual delivery of a high flow of oxygen into the loop 12 from the make-up valve 200. As a result, the randomness of the $O_2$ flush event is removed and can only be performed when the loop 12 is configured for the event after having received a request from the anesthesiologist.

Bellows

With reference again to FIG. 2, the construction of the bellows 212 of this invention is illustrated in detail. As noted above, the bellows 212 acts as a capacitor or buffer for storing gas exhaled from the lungs and returning it back to the lungs during inflation.

In the presently preferred embodiment, the hollow interior 210 of bellows 212 is connected by a tube 214 to the circulation loop 12. The bellows 212 is housed within a rigid casing 216 open to atmosphere, and a base 218 formed with an opening 220 and spaced bores 221. Weights 222 are connected by a support 223 to the bottom of the bellows 212 through opening 220 in the base 218 of casing 216 to counteract the sub-ambient atmosphere within the bellows interior 210 created by the suction exerted at the inlet of blower 36. The base 218 of casing 216 mounts a microswitch 224 in position to engage the bottom of bellows 212. As shown schematically in FIG. 1, the microswitch 224 is connected by a line 226 to the controller 34. Additionally, a linear optical encoder 228 is connected to the bellows 212 via the weight support 223, for purposes described below. The linear optical encoder 228 is connected by a line 230 to the control 34, and is preferably of a type commercially available from Hewlett Packard of San Jose, Calif., under Model No. HP HEDS-9200.

One purpose of the bellows 212 is to provide a collapsible volume on the suction side of blower 36 from which gas can be shifted into the patient's lungs 24, 28 during mechanical inspiration. Additionally, the bellows 212 provides a means to obtain a measurement or indication of the volume of gas within the circulation loop 12 to maintain isovolumetric operation of the system 10 wherein gas consumption of the patient is compensated for by the introduction of fresh gases into the loop 12. Isovolumetric operation is obtained as follows. The magnitude of weights 222 connected to bellows 212 is preferably chosen to cause the bottom of the bellows 212 to stay at a predetermined baseline position, spaced from the base 218 of casing 216, at the end of expiration. When the circuit volume decreases, the pressure distribution within the circulation loop 12 for a given speed of blower 36 and a given setting of proportional control valve 132 causes a lowering of the pressure at the bellows 212. In turn, the bellows 212 moves upwardly from the baseline position depicted in FIG. 2. If the bellows 212 fails to return to its baseline position at end exhalation, the linear optical encoder 228 sends a signal to the control 34 which opens valves 200, 202. The proportional flow control valves 200, 202 are controlled to introduce fresh gas into the circuit 12 at a total flowrate proportional to the distance of the bottom of the bellows 212 from its baseline position, until eventually the bottom of the bellows 212 returns to such baseline position.

As noted above and depicted in FIG. 2, the baseline position of the bottom of the bellows 212 is offset from the base 218 of the casing 216 which mounts the microswitch 224. The microswitch 224 is employed to reinitialize the linear encoder 228 whenever the bellows "bottoms out" and touches the casing base 218, thus triggering the microswitch 224.

Room Air Entrainment Valve

As noted above, one disadvantage associated with many closed ventilators and/or anesthesia delivery systems is their inability to operate without a supply of compressed gas either from the main hospital supply or from cylinders. This problem is overcome in the system 10 of this invention by providing a room air entrainment valve 230 within circulation loop 12 immediately upstream from the intake side of the blower 36. In the event of a catastrophic failure of the hospital gas supply, and an unavailability of compressed gas from separate tanks, the controller 34 is operative via line 232 to open the valve 230 and permit ventilation of the patient with room air entrained by the blower suction until the emergency can be corrected.

Oxygen Supply

Figure 6:
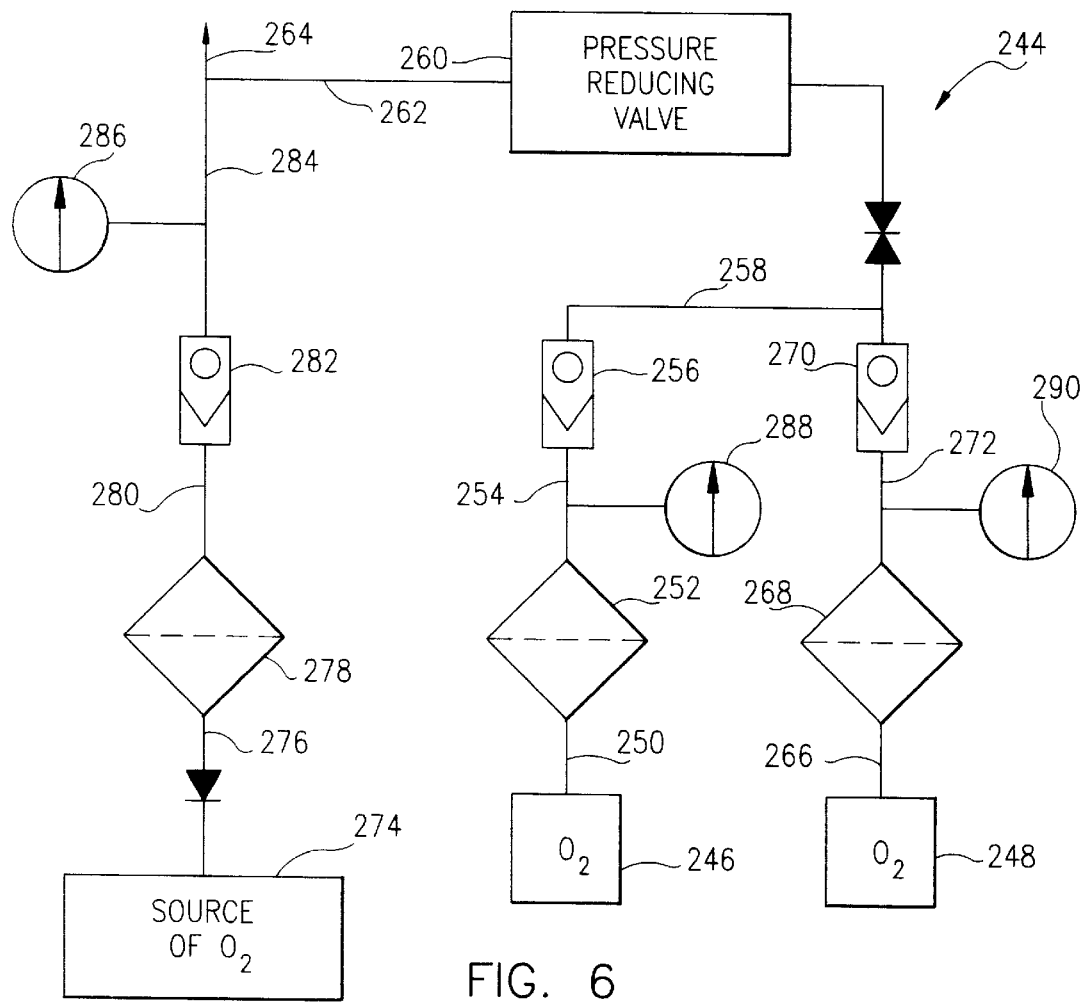
FIG. 6 is a block diagram depiction of the oxygen supply to the anesthesia delivery system.

With reference to FIG. 6, a schematic depiction of an oxygen supply circuit 244 is provided which is intended to provide oxygen to the gas make-up valve 200. In the "double yoke" system depicted in FIG. 6, two oxygen cylinders 246 and 248 are employed to provide a safety factor in the event one of the cylinders 246, 248 becomes low. Cylinder 246 is connected by a line 250 to a filter 252, which, in turn, is connected by a line 254 to a one-way valve 256. The one-way valve 256 is connected to a common line 258 leading to a pressure reducing valve 260 connected via line 262 to an $O_2$ supply line 264. Similarly, the second cylinder 248 is connected by a line 266 to a filter 268 which connects to a one-way valve 270 via line 272. The one-way valve 270 associated with cylinder 248, in turn, is connected to common line 258 leading to pressure reducing valve 260.

In addition to the oxygen cylinders 246, 248, oxygen is introduced to the $O_2$ supply line 264 from a source 274, e.g. the pipe line source of the hospital, through a flow path defined by line 276, filter 278, line 280, one-way valve 282 and a connector line 284 as depicted in FIG. 10. A pressure gauge 286 is mounted to the connector line 284 to monitor the pressure of the oxygen from source 274, which is nominally 50 psig for most hospital supply systems.

Although oxygen is normally supplied to the system 10 via source 274, the $O_2$ cylinders 246, 248 become important in the event of a disruption in such supply. As such, it is important for the anesthesiologist to have a means of accurately determining the quantity of oxygen within cylinders 246, 248. This capability is obtained in the circuit 244 of FIG. 10 by positioning a pressure gage 288 between the one-way valve 256 and cylinder 246, and a pressure gauge 290 between the one-way valve 270 and cylinder 248.

The advantage of locating pressure gauges 288, 290 in the position shown in FIG. 6 is best understood by comparison to known $O_2$ supply systems. In prior oxygen delivery systems, the pressure gauge is located downstream from the one-way valves connected to the $O_2$ cylinders. After opening an $O_2$ cylinder to obtain a pressure reading, the one-way valve prevents venting of the line connected to the pressure transducer or gauge, thus causing it to display the initial pressure reading. If the pipeline source of oxygen remains connected, the reading on the cylinder pressure gauge remains the same even if a full $O_2$ cylinder was replaced with an empty one in the same line. This is because, as noted above, substantially constant pressure is maintained between the one-way valve and pressure gauge.

This problem of potentially false readings of the content of oxygen cylinders is avoided in this invention by positioning each of the pressure gauges 288, 290 between their respective one-way valves 256, 270 and cylinders 246, 248. When one or the other of the cylinders 246, 248 is removed from the system, the pressure gauges 288, 290 are fully exhausted and return to a "0" reading. As a result, the sequence for reading the pressure of O2 cylinder 246, for example, consists simply of opening the cylinder 246 and then closing it while looking at the reading on pressure gauge 288. Both cylinders 246, 248 can be opened simultaneously and accurately read since the one-way valves 256 and 270 prevent transfilling of the cylinders via the common line 258.

The pressure reducing valve 260 operates, in effect, as a one-way valve and will only let gas flow in a direction from the cylinders 246, 248 to the $O_2$ supply line 264. The pressure reducing valve 260 is set to deliver oxygen from cylinders 246, 248 at a nominal pressure of 40 to 45 psig, but pipeline gas from source 274 (nominally at 50 psig) is prevented from flowing to the cylinders 246, 248 by the pressure reducing valve 260.

System Operation

The system 10 of this invention is highly versatile and can be utilized solely as a ventilation device in intensive care units and the like, or as an anesthesia delivery system in operating rooms. Different features of the system 10 are primarily intended for one or the other modes of operation, and other system elements are utilized in all modes of operation. For purposes of the present discussion, the operation of system 10 is first described in connection with its use as a ventilator, and then various modes of operation are explained when the system 10 delivers anesthesia to a patient during a surgical procedure.

Ventilator Operation

Ventilation is the process of bringing oxygen into the alveoli of the lungs, and washing out carbon dioxide from the lungs. In the absence of injury, disease or other conditions interfering with the normal breathing of a patient, the system 10 of this invention is operative to assist the patient with his or her own spontaneous ventilation. As noted above, the term "spontaneous ventilation" refers to inhalation and exhalation which is initiated solely by the patient. Although the system 10 can be configured to ventilate a patient mechanically, i.e. without any participation on the part of the patient, mechanical ventilation provided by system 10 is explained in the sections which follow because it is commonly used, and, in fact a requirement, with patients under general anesthesia.

The goal of the system 10 in assisting spontaneous ventilation of the patient is to reduce the "work of breathing," i.e. the effort which the patient's diaphragm and muscles must undertake to inspire and exhale a breath. When the system 10 is operated as a ventilator, oxygen is supplied through the gas make-up valve 200 and air or nitrogen is supplied through gas make-up valve 202.

As discussed above, an important aspect of this invention is the provision of pressure measurements at the distal tip 32 of endotracheal tube 16 which provide a much more accurate indication of the actual pressure within lungs 24, 28 than is possible using pressure sensors located at other positions along the circulation loop 12. Readings or measurements of the pressure within the lungs 24, 28 provides data for a feedback loop within the controller 34 which employs a PID control algorithm to govern the operation of proportional flow control valve 132 during spontaneous assisted ventilation. Such control proceeds as follows. A mixture of oxygen and air is circulated by the blower 36 around the circulation loop 12 past the Y-piece 14 and endotracheal tube 16. In order to assist the patient in taking a breath, feedback signals generated by inputs from the pressure transducer 108 cause the profiled plug 188 of proportional flow control valve 132 to move closer to the discharge end 186 of inlet tube 184, thus reducing the effective cross-sectional area of discharge end 186 and creating a back pressure within the circulation loop 12 between the proportional flow control valve 132 and the Y-piece 14. This back pressure shunts the flow of gas upstream from the Y-piece 14 into the endotracheal tube 16 and, hence, into the patient's lungs 24, 28. When the patient begins to exhale, the controller 34 operates the proportional flow control valve 132 causing its profiled plug 188 to move away from the discharge end 186 of inlet tube 184, thus inducing a suction within the circulation loop 12 at the Y-piece 14 which assists in removing the inhaled gas from the patient's lungs 24, 28.

The movement of the profiled plug 188 with respect to the discharge end 186 of proportional flow control valve 132 is governed by signals generated by the flow sensor 100. The flow sensor 100 is effective to sense the direction of flow into the endotracheal tube 16, as the patient inhales, and then to sense movement of the gas in the opposite direction which is exhaled by the patient through the endotracheal tube 16. Signals from the flow sensor 100 representative of the direction of movement of gas within the endotracheal tube 16 are transmitted via line 102 and the flow/pressure monitor 104 to controller 34, as described above. The movement of the profiled plug 188 relative to the discharge end 186 of proportional flow control valve 132 is also a function of the magnitude of the pressure sensed at the distal tip 32 of endotracheal tube 16.

Consequently, the pressure of the distal tip 32 of the endotracheal tube 16 is controlled by the proportional flow control valve 132 to ensure the desired tidal volume of gas is introduced into the patient's lungs with as little work from the patient as possible, during each breath.

Anesthesia Delivery

As noted above, general anesthesia depresses the central nervous system and is preferred for major surgeries. The muscles become relaxed to the point where the patient cannot breathe on his or her own, and therefore the anesthesia delivery system 10 must mechanically ventilate the patient and function, for all practical purposes, as a life support system. The controller 34 monitors essentially every aspect of the system operation and controls various elements within the circulation loop 12 to deliver the desired intermixture of oxygen, nitrous oxide and volatile anesthetics in a predetermined tidal volume over a set inspiration time to maintain the patient anesthetized during the surgery. Additionally, as discussed in more detail below, the controller 34 is effective to operate the proportional flow control valve 132 using PID control algorithms to deliver particular inspiratory flow rate waveforms to the patient, depending upon the condition of the patient's lungs.

Initially, the controller 34 is programmed to deliver the desired tidal volume having a given inspiration time, with or without an inspiratory pause, at a pressure which is commensurate with the condition of the patient's lungs. For example, patients having lungs with low compliance require a higher pressure within circulation loop 12 compared to patients having lungs with normal compliance. As noted above, the maximum or "shut-off" pressure which can be generated by the blower 36 is a function of its rotational speed. Preferably, the default blower speed is set so that the maximum pressure that can be generated within the circuit 12 is 20 cm $H_2O$. This default setting can be overridden by the anesthesiologist so that the pressure within circulation loop 12 can be increased to 150 cm/$H_2O$ for patients having lungs of particularly low compliance.

Steady state operation of the system 10 during mechanical ventilation requires control of the following:

(1) Concentration of anesthetics;
(2) Concentration of oxygen;
(3) Volume of gas within circulation loop 12;
(4) Pressure at specific points within circulation loop 12, e.g. at the Y-piece 14;
(5) An $O_2$ flush event;
(6) Proper operation of the scavenging system;
(7) Maintenance of proper humidity and temperature of gas circulating within loop 12; and
(8) Monitoring of end tidal carbon dioxide concentration.

All of these various control functions impact upon the proper operation of system 10 during mechanical ventilation.

Considering first the introduction of gases into the circulation loop 12, and the maintenance of appropriate concentrations of various gases, the multi-gas analyzer 120 is effective to provide real time measurements of the concentrations of carbon dioxide, oxygen, nitrous oxide and volatile anesthetics. As noted above, the sampling port 122 of the multi-gas analyzer 120 is located at the distal tip 32 of endotracheal tube 16, near the carina 30 of the patient, thus enabling it to provide measurements of gas concentrations at the lungs without the influence of gases circulating within the loop 12. Signals from the multi-gas analyzer 120 are provided to the controller 34 which includes PID control algorithms effective to control the operation of syringe pump 40, and valves 200, 202, such that they open and close to introduce the required amount of volatile anesthetic, oxygen and nitrous oxide, respectively, into the circulation loop 12. It is noted that the syringe pump 40 introduces a liquid volatile anesthetic into loop 12, but because of the positioning of syringe pump 40 immediately downstream from the blower 36 and upstream from the bacterial filter 46, there is an extremely remote chance that any volatile anesthetic in liquid form would be introduced directly into the patient's lungs.

It is contemplated that once the relative concentrations of oxygen, nitrous oxide and volatile anesthetic have been achieved within circulation loop 12 then the controller 34 will operate to introduce constant, proportionate quantities of each material without the need for significant feedback correction. For example, if the desired ratio of nitrous oxide to oxygen is 70% to 30%, accompanied by a small amount of volatile anesthetics, fresh quantities of these gases and liquid can be introduced into the loop 12, as required, in those same proportions.

In order to maintain a constant volume within circulation loop 12, i.e. to account for use of gas by the patient, the controller 34 receives signals from the linear optical encoder 228 associated with the bellows 212. As described in detail above, the bellows 212 acts essentially as a capacitor, storing gas exhaled from the lungs during exhalation and returning it back to the lungs during inhalation. The signals received by the controller 34 from the linear encoder 228 are representative of the distance of the bellows 212 from its baseline position, and fresh gas is introduced into the circuit 12 from valves 200, 202 at a total flowrate proportional to such distance. When the bellows 212 bottoms out and triggers microswitch 224, the linear encoder 228 is reinitialized.

Another important aspect of the operation of system 10 in the mechanical ventilation mode is the manner in which the appropriate volume of gas is introduced into the patient's lungs over a desired inspiration time, with or without an inspiratory pause. As a practical matter, the proportional flow control valve 132 functions as a ventilator within the circulation loop 12. The profiled plug 188 of proportional flow control valve 132 is movable to create a back pressure or suction within the circulation loop 12 in the area of Y-piece 14. In order to mechanically induce inspiration on the part of the patient, the controller 34 causes the profiled plug 188 of proportional flow control valve 132 to move toward the discharge end 186 of tube 184 thus creating pressure at Y-piece 14. This shunts flow from the Y-piece 14 into the endotracheal tube 16 to the patient's lungs, 24, 28. Flow and pressure are monitored by the flow sensor 100 and pressure transducer 108, respectively, to provide any desired correction in the control of the operation of proportional flow control valve 132.

As noted above, the system 10 of this invention has the ability to deliver a variety of different modes of mechanical ventilation. The controller 34 is effective to operate proportional flow control valve 132 and blower 36 to obtain high frequency ventilation (HFV), and to produce continuous flow apneic ventilation (CFAV), as described above.

Additionally, the controller 34 is effective to operate proportional flow control valve 132, using pressure or flow rate feedback loops, to provide pressure or flow rate inspiratory waveforms having different configurations to achieve equal distribution of ventilation in lungs having unequal time constants. Details of the methodology of inspiratory waveform shaping, and a unique lung classification scheme, are provided in U.S. patent application Ser. No. 08/546,301, filed Oct. 20, 1995 entitled "Lung Classification Scheme, A Method of Lung Class Identification And Inspiratory Waveform Shapes", to Lampotang, et al. which is owned by the assignee of this invention, and the disclosure of which is incorporated by reference in its entirety herein.

Inspiratory flowrate waveform shaping is achieved in the system 10 of this invention by operation of the proportional flow control valve 132, appropriately controlled by the controller 34 using a feedback loop including the flow sensor 100 and a PID control algorithm within the controller 34. Depending upon the particular inspiratory flowrate waveform chosen, the controller 34 is operative to move the profiled plug 188 of proportional flow control valve 132 at a selected speed and distance relative to the discharge opening 186 of tube 184 associated with valve 132. The flow sensor 100 acts as a feedback sensor to sense the flowrate at the proximal end 31 of endotracheal tube 16 and transmit a signal to the PID control algorithm at the controller 34 which functions to compare the actual flowrate with the desired inspiratory flowrate. An "error" or correction signal is produced by the PID control algorithm which is input to the proportional flow control valve 132 so that movement of its profiled plug 188 is corrected, if required, to obtain the desired inspiratory flowrate waveform.

An inspiratory "pressure" waveform can also be delivered by system 10 in the same fashion, except with a feedback loop including signals from the pressure transducer 108 at the distal tip 32 of endotracheal tube 16 and another PID control algorithm within controller 34. In either case, the goal is to precisely control the movement of profiled plug 188 within proportional flow control valve 132 to obtain pressure and suction at the Y-piece 14, which, in turn, results in the introduction of a selected volume of gas in a predetermined inspiration time having a "shape", or pressure over time, which provides the best ventilation distribution for that patient's lungs, while minimizing mean lung pressure.

The proportional flow control valve 132 can also be utilized as a positive end expiratory pressure (PEEP) valve, if needed. For example, the compliance of the lungs of certain patients is such that it is desirable to maintain the pressure within the lungs somewhat above ambient upon exhalation to avoid undue collapse of the lungs. If the lungs are allowed to collapse to a certain extent in such patients, it may be difficult and require additional work to then inflate the lungs during inhalation. In such cases, the controller 34 is effective to control the movement of the profiled plug 188 of proportional flow control valve 132 so that when a selected pressure is reached during exhalation the profiled plug 188 moves to prevent further escape of gas from the patient's lungs and thus maintains the desired pressure therein.

In addition to mechanical ventilation, the system 10 of this invention is capable of allowing for manual ventilation of the patient. In this mode of operation, the controller 34 opens purge valve 130, and the manual bag 92 is then used by the anesthesiologist to ventilate the patient. It should be understood that while the manual bag 92 is primarily available for manual ventilation, it nevertheless remains connected to the circulation loop 12 regardless of the mode of ventilation of system 10. As a result, the manual bag 92 provides a visual indication of respiration as it expands and retracts, and also can be employed by the anesthesiologist to obtain a tactile sense of the compliance of the patient's lungs at all times during ventilation.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

For example, the positive pressure source 300 and negative pressure source 302 are described below as being functionally provided by a single fixed speed or variable speed, centrifugal blower 36. It is contemplated that the blower 36 could be replaced with an individual positive pressure source 300 such as a compressor, and a negative pressure source 302 such as a vacuum pump, which is considered within the scope of this invention.

Therefore, it is intended that the invention not be limited to the particular embodiment disclosed as the best mode contemplated for carrying out this invention, but that the invention will include all embodiments falling within the scope of the appended claims.

What is claimed is:

1. Apparatus for use as a ventilator and/or an anesthesia delivery system, comprising:
   a circulation loop connectable to an airway device to which a patient can be connected;
   a source of positive pressure and a source of negative pressure which are collectively operative to circulate a flow of gas within said circulation loop;
   a control device having a variable-size orifice, said control device being located in said circulation loop between said airway device and said source of negative pressure;
   a controller operatively connected to said control device, said controller being effective to selectively cause said variable-size orifice of said device to alternatively create a pressure at said airway device which permits gas to flow into said airway device, and then a pressure at said airway device which permits gas to flow out of said airway device.

2. The apparatus of claim 1 in which said source of positive pressure and said source of negative pressure are collectively comprised of a centrifugal blower having a negative pressure, intake side and a positive pressure, exhaust side.

3. The apparatus of claim 1 in which said control device is a proportional flow control valve having said variable-size orifice.

4. The apparatus of claim 3 in which said proportional control valve includes:
   (i) a valve body having a hollow interior, an inlet and an outlet;
   (ii) a conduit extending from said inlet of said valve body into said interior thereof, said conduit being formed with a discharge opening having a cross sectional area; and
   (iii) a valve closure member movable with respect to said conduit to vary the effective cross sectional area of said discharge opening thereof.

5. The apparatus of claim 4 in which said valve closure member comprises a woofer speaker including a diaphragm which mounts a profiled plug having a tapered outer wall whose diameter progressively increases from the tip thereof to a diameter at least equal to the diameter of said discharge opening of said conduit, said diaphragm of said woofer speaker being effective to move said profiled plug toward and away from said discharge opening of said conduit.

6. Apparatus for use as a ventilator and/or an anesthesia delivery system, comprising:
   a circulation loop connectable to an airway device to which a patient can be connected;
   a blower operative to circulate a flow of gas within said circulation loop, said blower having an intake side and an exhaust side;
   a proportional flow control valve located in said circulation loop between said airway device and the intake side of said blower;
   a gas storage reservoir located in said circulation loop between said proportional flow control valve and the intake side of said blower;
   a controller operatively connected to said proportional flow control valve, said controller being effective to selectively move said proportional flow control valve to a position to alternatively create a pressure at said airway device which permits gas to flow into said airway device, and then a pressure at said airway device which permits gas to flow out of said airway device.

7. The apparatus of claim 6 in which said gas storage reservoir includes a collapsible bellows.

8. Apparatus for use as a ventilator and/or an anesthesia delivery system, comprising:
   an endotracheal tube for intubating a patient, said endotracheal tube having a proximal end and a distal tip which is positionable near the carina of a patient;
   a circulation loop connectable to said endotracheal tube;
   a blower operative to circulate a flow of gas within said circulation loop, said blower having an intake side and an exhaust side;
   a pressure sensor operative to produce a signal representative of the pressure at said distal tip of said endotracheal tube;
   a proportion flow control valve located in said circulation loop between said endotracheal tube and the intake side of said blower; and
   a controller operatively connected to said proportion flow control valve, said controller being effective in response to receipt of said signal from said pressure sensor to selectively move said proportion flow control valve to a position to alternatively create a pressure at said proximal end of said endotracheal tube which permits gas to flow into said endotracheal tube and then a pressure at said proximal end which permits gas to flow out of said endotracheal tube.

9. The apparatus of claim 8 in which said blower is selected from the group consisting of a variable speed, centrifugal blower and a fixed speed blower.

10. The apparatus of claim 8 in which said pressure sensor includes a lumen connected to said distal tip of said endotracheal tube, and a pressure transducer connected by a line to said lumen, said pressure transducer being effective to produce said signal representative of the pressure at said distal tip.

11. The apparatus of claim 8 further including a Y-piece interconnecting said circulation loop with said endotracheal tube, and at least one other flow/pressure sensor located at said Y-piece to provide an independent measurement of pressure thereat.

12. Apparatus for use as a ventilator and/or an anesthesia delivery system, comprising:
   a circulation loop connectable to an airway device to which a patient can be connected;
   a blower operative to circulate a flow of intermixed oxygen, a second gas and at least one anesthetic within said circulation loop;
   a multi-gas sensor having an input located at a distal tip of a endotracheal tube, said multi-gas sensor being effective to sense the presence of oxygen, anesthetic gas, carbon dioxide and other gases within said flow and produce signals representative of the concentration of each gas;
   first, second and third supply means for introducing oxygen, said second gas and said at least one anesthetic, respectively, into said circulation loop;
   a controller operatively connected to each of said first, second and third supply means and to said multi-gas sensor, said controller being effective upon receipt of said signals from said multi-gas sensor to selectively control the operation of said first, second and third supply means to obtain the desired, relative concentration of oxygen, said second gas and said at least one anesthetic within said circulation loop.

13. The apparatus of claim 12 in which said first supply means is a gas make-up valve connected to said circulation loop, said gas make-up valve being adapted to connect to a source of oxygen.

14. The apparatus of claim 12 in which said second supply means is a gas make-up valve connected to said circulation loop, said gas make-up valve being adapted to connect a source of clinically usable gas such as nitrous oxide, nitrogen and helium.

15. The apparatus of claim 12 in which said third supply means is a motorized anesthetic syringe pump connected to said circulation loop, said syringe pump including:
   a pump body having an interior carrying a movable plunger;
   a needle connected at one end to said interior of said pump body;
   a sintered metal insert carried within a copper block located in said circulation loop, said needle being connected to said sintered metal insert to deliver liquid anesthetic therein where it is vaporized and carried by said circulation loop to the patient's lung.

16. Apparatus for use as a ventilator and/or an anesthesia delivery system, comprising:
   a circulation loop connectable to an airway device to which a patient can be connected;
   a blower operative to circulate a flow of gas within said circulation loop;
   a supply device for introducing gas into said circulation loop;
   a bellows having a hollow interior communicating with said circulation loop, said bellows being movable from a baseline position when the volume of gas within said circulation loop changes;
   a sensor device for sensing the extent of movement of said bellows from said baseline position, and for producing a signal representative of said movement;
   a controller operatively connected to said supply device, said controller being effective in response to receipt of said signal from said sensor device to open said supply device so that fresh gas is introduced into said circulation loop at a total flowrate proportional to the extent of movement of said bellows from said baseline position.

17. The apparatus of claim 16 in which said supply device is a gas make-up valve adapted to connect to a source of clinical gas, and a gas make-up valve adapted to connect to a source of oxygen.

18. The apparatus of claim 16 in which said supply device is a gas make-up valve adapted to connect to a source of oxygen, a gas make-up valve adapted to connect to a source of clinical gas, and, a motor-driven anesthetic syringe pump containing a volatile anesthetic.

19. The apparatus of claim 16 in which said bellows is formed with a bottom wall and a hollow interior connected to said circulation loop, said bellows being received within a casing having a sidewall connected to a base formed with an opening, said bellows being connected to at least one weight.

20. The apparatus of claim 19 in which said sensor device is a linear optical encoder operative to sense the extent of movement of said bellows from said baseline position and produce said signal, and a microswitch mounted to said base of said casing in position offset from said baseline position of said bellows, said microswitch being triggered in the event said bellows bottoms out against said base of said casing to reinitialize said linear optical encoder.

21. Apparatus for use as a ventilator and/or anesthesia delivery system, comprising:
   a circulation loop connectable to an airway device to which a patient can be connected;
   a blower operative to circulate a flow of gas within said circulation loop;
   a supply for introducing gas into said circulation loop;
   a heating/cooling device for selectively heating or cooling the gas circulating within said circulation loop, said heating/cooling device including at least one temperature sensor operative to sense the temperature thereof and produce a signal representative of said temperature;
   a controller operatively connected to said heater/cooler device and to said temperature sensor thereof, said controller being effective to operate said heater/cooler device to heat the circulating gas and adjust the heating operation thereof dependent on said signal, said controller being effective to operate said heater/cooler device to cool the circulating gas and adjust the cooling operation thereof dependent on said signal.

22. The apparatus of claim 21 in which said heating/cooling device comprises:
   a housing having a hollow interior;
   a core including a plurality of interconnected fins formed of a thermally conductive material, said core being mounted within said hollow interior of said housing;
   a number of thermo-electric Peltier modules connected to said core, said Peltier modules being effective to heat or cool said core dependent on the direction of flow of electrical current therethrough;
   at least one temperature sensor connected to said core.

23. The apparatus of claim 22 in which said controller is operative to direct electrical current through said Peltier modules of said heating/cooling device in a first direction to heat said core and the gas flowing therethrough, said controller being operative to direct electrical current through said Peltier modules of said heating/cooling device in a second direction to cool said core and the gas flowing therethrough.

24. Apparatus for use as a ventilator and/or an anesthesia delivery system, comprising:
- a circulation loop connectable to an airway device to which a patient can be connected;
- a blower operative to circulate a flow of gas within said circulation loop, said blower having an intake side and an exhaust side;
- a purge valve connected to said circulation loop downstream from the airway device, said purge valve being movable between an open position wherein gas is discharged from said circulation loop, and a closed position;
- a proportional flow control valve located in said circulation loop between said purge valve and the intake side of said blower, said proportional flow control valve including:
  - (i) a valve body having a hollow interior, an inlet and an outlet;
  - (ii) a conduit extending from said inlet of said valve body into said interior thereof, said conduit being formed with a discharge opening having a cross sectional area; and
  - (iii) a valve closure member movable with respect to said conduit to vary the effective cross sectional area of said discharge opening thereof;
- a controller operatively connected to said proportional flow control valve, said controller being effective to move said valve closure member in a direction toward said discharge opening of said conduit to reduce the effective cross sectional area thereof and create a pressure at the airway device which permits a flow of gas into the airway device, said controller being effective to move said valve closure member in a direction away from said discharge opening of said conduit to increase the effective cross sectional area thereof and create a pressure at the airway device to permit a flow of gas out of the airway device.

25. The apparatus of claim 24 in which said valve closure member comprises a woofer speaker including a diaphragm which mounts a profiled plug having a tapered outer wall whose diameter progressively increases from the tip thereof to a diameter at least equal to the diameter of said discharge opening of said conduit, said diaphragm of said woofer speaker being effective to move said profiled plug toward and away from said discharge opening of said conduit in response to signals from said controller.

26. The apparatus of claim 25 in which a donut-shaped seal formed of flexible material is mounted to said woofer diaphragm in a position to engage said discharge opening of said conduit.

27. The apparatus of claim 24 further including a room air entrainment valve connected to said circulation loop at the intake side of said blower, said room air entrainment valve being movable to an open position to permit entrainment of ambient air by said blower into said circulation loop.

28. The apparatus of claim 24 further including a purge valve comprising:
- a valve body having an inlet communicating with said circulation loop, and an outlet;
- a flexible diaphragm movable with respect to said outlet of said valve body; and
- means for moving said diaphragm between a closed position against said outlet, and an open position spaced from said outlet.

29. The apparatus of claim 28 in which said means for moving said diaphragm includes a pilot valve connected by a line to said valve body of said purge valve, and a pressure regulator connected to said pilot valve and to a source of pressurized gas, said pilot valve being effective to transmit pressurized gas from the source into said valve body to move said flexible diaphragm to said closed position and to vent pressurized gas from said valve body to allow said flexible diaphragm to move to said open position.

30. In an apparatus for use as a ventilator and/or anesthesia delivery system including an airway device to which a patient can be connected, a proportional flow control valve comprising:
- a valve body having a hollow interior, an inlet and an outlet, said inlet of said valve body communicating with a source of gas and the airway device;
- a conduit extending from said inlet of said valve body into said interior thereof, said conduit being formed with a discharge opening having a cross sectional area; and
- a valve closure member movable with respect to said conduit to vary the effective cross sectional area of said discharge opening thereof, said valve closure member being movable in a direction toward said discharge opening of said conduit to reduce the effective cross sectional area thereof and create a pressure at the airway device which permits a flow of gas from the source into the airway device, and said valve closure member being movable in a direction away from said discharge opening of said conduit to increase the effective cross sectional area thereof and create a pressure at the airway device to permit a flow of gas out of the airway device.

31. The proportional flow control valve of claim 30 in which said valve closure member comprises a woofer speaker including a diaphragm which mounts a profiled plug having a tapered outer wall whose diameter progressively increases from the tip thereof to a diameter at least equal to the diameter of said discharge opening of said conduit, said diaphragm of said woofer speaker being effective to move said profiled plug toward and away from said discharge opening of said conduit.

32. The proportional flow control valve of claim 31 in which a donut-shaped seal formed of flexible material is mounted to said diaphragm in a position to engage said discharge opening of said conduit.

33. Apparatus for use as a ventilator and/or an anesthesia delivery system, comprising:
- a circulation loop connectable to an airway device to which a patient can be connected;
- a blower operative to circulate a flow of gas within said circulation loop;
- a purge valve connected to said circulation loop downstream from the airway device, said purge valve being movable between an open position wherein gas is discharged from said circulation loop, and a closed position;
- a scavenging system connected by a discharge line to said purge valve, said scavenging system including:
  - (i) a manifold having an inlet connected to said discharge line, and an outlet;
  - (ii) a sensor device for producing a signal representative of the pressure within said manifold; and
  - (iii) a proportional flow control valve connected to said manifold between said inlet and said outlet thereof, said proportional flow control valve being proportionately movable between open and closed positions;
- a controller operatively connected to said proportional flow control valve and to said sensor device said controller being effective in response to receipt of said signal from said sensor device to selectively move said proportional flow control valve between said open and closed positions to maintain a substantially constant pressure within the manifold.

34. The apparatus of claim 33 in which said sensor device is a pressure transducer.

35. The apparatus of claim 33 in which said proportional flow control valve comprises:
   a valve body having a hollow interior formed with an inlet connected to said manifold, and an outlet downstream from said inlet;
   a conduit extending from said inlet into said interior of said valve body, said conduit being formed with a discharge opening having a cross sectional area;
   a valve closure member movable with respect to said conduit to vary the effective cross sectional area thereof.

36. The apparatus of claim 35 in which said valve closure member comprises a woofer speaker including a diaphragm which mounts a profiled plug having a tapered outer wall whose diameter progressively increases from the tip thereof to a diameter at least equal to the diameter of said discharge opening of said conduit, said diaphragm of said woofer speaker being effective to move said profiled plug toward and away from said discharge opening of said conduit in response to signals from said controller.

37. The apparatus of claim 36 in which a donut-shaped seal formed of flexible material is mounted to said diaphragm in position to engage said discharge opening of said conduit.

38. The apparatus of claim 33 in which said scavenging system further includes a scavenging bag connected to said manifold between said inlet thereof and said proportional flow control valve.

39. The apparatus of claim 33 in which said scavenging system further includes a gravity pressure relief valve, and a gravity vacuum relief valve, both connected to said manifold.

40. The apparatus of claim 33 in which said scavenging system further includes a tube having an inlet connected to said manifold, and an outlet covered by a removable cap.

41. Apparatus for use as a ventilator and/or an anesthesia delivery system, comprising:
   a circulation loop connectable to an airway device with which a patient can be intubated;
   a blower operative to circulate a flow of gas within said circulation loop;
   oxygen supply device for introducing oxygen into said circulation loop, including:
      (i) at least one tank containing oxygen;
      (ii) a gas make-up valve connected to said recirculation loop;
      (iii) a transfer line interconnecting said tank and said gas make-up valve, said transfer line mounting a one-way valve and a pressure reducing device for supplying oxygen to said transfer line at a predetermined pressure, said pressure reducing device being located between said gas make-up valve and said one-way valve;
      (iv) a pressure gauge connected to said transfer line between said one-way valve and said tank;
   a controller operative to open and close said gas make-up valve to selectively introduce oxygen into said circulation loop.

42. The apparatus of claim 41 in which said pressure reducing device is a pressure reducing one-way valve, said valve permitting the flow of oxygen only in a direction from tank to said gas make-up valve.

43. The apparatus of claim 41 in which said oxygen supply device further includes:
   a primary oxygen supply including a supply line having one end connected to said transfer line and an opposite end adapted to connect to a source of oxygen;
   a one-way valve connected to said supply line; and
   a pressure gauge connected to said supply line between said transfer line and said one-way valve.

44. The apparatus of claim 41 in which said oxygen supply device further includes:
   first and second oxygen tanks each connected by a feed line to said transfer line;
   each of said feed lines mounting a one-way valve and a pressure gauge, each of said pressure gauges being positioned in a respective feed line between an oxygen tank and a one-way valve.

45. An anesthetic delivery system, comprising:
   a circulation loop connectable to an endotracheal tube with which a patient can be intubated, said endotracheal tube having a proximal end and a distal tip which is positionable near the carina of the patient;
   a blower operative to circulate a flow of gas within said circulation loop, said blower having an intake side and an exhaust side;
   a supply device for introducing a volatile anesthetic into said circulation loop, said supply device being located at the exhaust side of said blower;
   a first device for introducing oxygen into said circulation loop, and second device for introducing another clinical gas into said circulation loop, said first and second device being located on the intake side of said blower;
   a carbon dioxide absorber connected to said circulation loop to receive the flow of gas therethrough, and means for permitting the flow of gas within said circulation loop to bypass said carbon dioxide absorber;
   a bacterial filter connected to said circulation loop between said blower and the endotracheal tube;
   a heater/cooler connected to said circulation loop;
   a manual breathing bag connected to said circulation loop upstream from the endotracheal tube;
   at least one pressure sensor located at said distal tip of said endotracheal tube, said pressure sensor producing a signal representative of the pressure at said distal tip;
   a multi-gas sensor having an input located at said distal tip of said endotracheal tube, said multi-gas sensor being effective to produce individual signals representative of the respective concentration of oxygen, volatile anesthetic, nitrous oxide and carbon dioxide within said flow of gas;
   a flow sensor located at said proximal end of said endotracheal tube, said flow sensor being effective to produce a first signal representative of the direction of flow of gas into or out of said endotracheal tube and a second signal representative of the magnitude of gas flow into or out of said endotracheal tube;
   a purge valve having an inlet connected to said circulation loop downstream from said endotracheal tube and an outlet, said purge valve being movable between an open position and a closed position;
   a scavenging system connected to said outlet of said purge valve;
   a proportional flow control valve located in said circulation loop between said purge valve and the intake side of said blower;

a bellows having a hollow interior communicating with said circulation loop, said bellows being located between said proportional flow control valve and the intake side of said blower;

a room air entrainment valve connected to said circulation loop at said intake side of said blower; and a controller operatively connected to said blower, said supply device, said first and second devices, said heater/cooler, said at least one pressure sensor, said multi-gas sensor, said flower sensor, said purge valve, said scavenging system, said proportional flow control valve and said room air entrainment valve.

46. The anesthesia delivery system of claim 45 in which said blower is a variable speed, centrifugal blower.

47. The anesthesia delivery system of claim 45 in which said pressure sensor includes a lumen connected to said distal tip of said endotracheal tube, and a pressure transducer connected by a line to said lumen, said pressure transducer being effective to produce said signal representative of the gas pressure at said distal tip.

48. The anesthesia delivery system of claim 45 further including at least one other pressure sensor located at a Y-piece which interconnects said circulation loop to said endotracheal tube to provide an independent measurement of pressure thereat.

49. The anesthesia delivery system of claim 45 in which each of said first and second device includes a gas make-up valve connected to said circulation loop, said gas make-up valves being operatively controlled by said controller.

50. The apparatus of claim 45 in which said third supply device is a motorized anesthetic syringe pump connected by a needle to a sintered metal insert carried by a copper block within said circulation loop, said syringe pump being effective to introduce volatile anesthetics in liquid form into said sintered metal insert where they are vaporized.

51. The apparatus of claim 45 in which said bellows is formed with a bottom wall and a hollow interior connected to said recirculation loop, said bellows being received within a casing having a sidewall which is connected to a base formed with an opening, said bottom wall of said bellows being connected to at least one weight.

52. The anesthesia delivery system of claim 51 further including sensor device including a linear optical encoder operative to sense the extent of movement of said bellows from said baseline position and produce said signal, and a microswitch mounted to said base of said casing in position offset from said baseline position of said bellows, said microswitch being triggered in the event said bellows bottoms out against said base of said casing to reinitialize said linear optical encoder.

53. The apparatus of claim 45 in which said heater/cooler comprises:

a housing having a hollow interior;

a core including a plurality of interconnected fins formed of a thermally conductive material, said core being mounted within said hollow interior of said housing;

a number of thermoelectric Peltier modules connected to said core, said Peltier modules being effective to heat or cool said core dependent on the direction of flow of electrical current therethrough;

at least one temperature sensor connected to said core.

54. The apparatus of claim 45 further including a purge valve including:

a valve body having an inlet communicating with said circulation loop, and an outlet;

a flexible diaphragm movable with respect to said outlet of said valve body; and means for moving said diaphragm between a closed position against said outlet, and an open position spaced from said outlet.

55. The apparatus of claim 54 in which said means for moving said diaphragm includes a pilot valve connected by a line to said valve body of said purge valve, and a pressure regulator connected to said pilot valve and to a source of pressurized gas, said pilot valve being effective to transmit pressurized gas from the source into said valve body to move said flexible diaphragm to said closed position and to vent pressurized gas from said valve body to allow said flexible diaphragm to move to said open position.

56. The anesthesia delivery system of claim 45 in which said proportional flow control valve includes:

a valve body having a hollow interior, an inlet and an outlet;

a conduit extending from said inlet of said valve body into said interior thereof, said conduit being formed with a discharge opening having a cross sectional area;

a valve closure member movable with respect to said conduit to vary the effective cross sectional area of said discharge opening thereof.

57. The apparatus of claim 56 in which said closure member comprises a woofer speaker including a diaphragm which mounts a profiled plug having a tapered outer wall whose diameter progressively increases from the tip thereof to a diameter at least equal to the diameter of said discharge opening of said conduit, said diaphragm of said woofer speaker being effective to move said profiled plug toward and away from said discharge opening of said conduit in response to signals from said controller.

58. The apparatus of claim 56 in which a donut-shaped seal formed of flexible material is mounted to said diaphragm in position to engage said discharge opening of said conduit.

59. The apparatus of claim 45 further including a room air entrainment valve connected to said circulation loop at the intake side of said blower, said room air entrainment valve being movable to an open position to permit entrainment of ambient air by said blower into said circulation loop.

60. The anesthesia delivery system of claim 45 in which said scavenging system includes:

(i) a manifold having an inlet connected to said discharge line, and an outlet;

(ii) a sensor device for producing a signal representative of the pressure within said manifold; and (iii) a proportional flow control valve connected to said manifold between said inlet and said outlet thereof, said proportional flow control valve being proportionately movable between open and closed positions.

61. The apparatus of claim 60 in which said proportional flow control valve comprises:

a valve body having a hollow interior formed with an inlet connected to said manifold, and an outlet downstream from said inlet;

a conduit extending from said inlet into said interior of said valve body, said conduit being formed with a discharge opening having a cross sectional area;

a valve closure member movable with respect to said conduit to vary the effective cross sectional area thereof.

62. The apparatus of claim 60 in which said scavenging system further includes a scavenging bag connected to said manifold between said inlet thereof and said proportional flow control valve.

63. The apparatus of claim 60 in which said scavenging system further includes a gravity pressure relief valve, and a gravity vacuum relief valve, both connected to said manifold.

64. The apparatus of claim 60 in which said scavenging system further includes a tube having an inlet connected to said manifold, and an outlet covered by a removable cap.

65. The anesthesia delivery system of claim 45 further including an oxygen supply device for introducing oxygen into said circulation loop, said oxygen supply device including:
  (i) at least one tank containing oxygen;
  (ii) a gas make-up valve connected to said recirculation loop;
  (iii) a transfer line interconnecting said tank and said gas make-up valve, said transfer line mounting a one-way valve and a pressure reducing means for supplying oxygen to said transfer line at a predetermined pressure, said pressure reducing means being located between said gas make-up valve and said one-way valve; and
  (iv) a pressure gauge connected to said transfer line between said one-way valve and said tank.

66. The apparatus of claim 65 in which said oxygen supply device further includes:
  first and second oxygen tanks each connected by a feed line to said transfer line;
  each of said feed lines mounting a one-way valve and a pressure gauge, each of said pressure gauges being positioned in a respective feed line between an oxygen tank and a one-way valve.

67. A method of ventilating a patient, comprising:
  providing a source of positive pressure and a source of negative pressure;
  circulating a flow of gas within a circulation loop connectable to a patient by an airway device with the positive and negative pressures, respectively;
  positioning a control device having a variable-sized orifice within the circulation loop between the patient airway device and the source of negative pressure;
  operatively connecting a controller to said control device and selectively using the controller to cause the variable-sized orifice to alternatively create a pressure at the airway device which permits a flow of gas into the airway device, and then a pressure at the airway device which permits gas to flow out of the airway device.

68. The method of claim 67 in which the step of using said controller with said variable-sized orifice comprises the step of operating a proportional flow control valve to create the flow of gas into, and the flow of gas out of the patient airway device.

69. A method of ventilating a patient, comprising:
  circulating a flow of gas within a circulation loop which is connectable to a patient by an airway device;
  sensing one of the pressure and flow rate within said circulation loop at said airway device, and producing a corresponding signal;
  controlling the operation of a variable-orifice control device, dependent on said signal, to alternatively direct a portion of the gas flow within the circulation loop through the airway device and into the lungs of the patient, and then permit gas to flow out of the patient's lungs and through the airway device into the circulation loop.

70. The method of claim 69 in which said step of circulating a flow of gas includes circulating a flow of gas within a circulation loop connected to an endotracheal tube having a distal tip positionable near the carina of a patient.

71. The method of claim 70 further including the step of sensing one of the flow and pressure of the gas at the distal tip of the endotracheal tube, and producing a corresponding signal.

72. The method of claim 71 in which said step of controlling a variable-orifice control device includes controlling the variable-orifice control device dependent on the signal.

73. The method of claim 69 in which said step of sensing one of the pressure and flow rate comprises sensing the flow rate within the circulation loop at said airway device during inspiration of the patient.

74. The method of claim 69 in which said step of sensing one of the pressure and flow rate comprises sensing the pressure within the circulation loop at said airway device during exhalation of the patient.

75. A method of ventilating a patient, comprising:
  circulating a flow of gas within a circulation loop connected to the proximal end of an endotracheal tube whose distal tip is located near the carina of the patient;
  sensing one of the pressure and flow rate of the gas at the distal tip of the endotracheal tube, and producing a signal representative thereof;
  controlling the operation of a proportional flow control valve mounted within the circulation loop, dependent on said signal, to alternatively direct a flow of gas into and out of the endotracheal tube.

76. The method of claim 75 in which said step of controlling the operation of a proportional flow control valve comprises;
  causing a valve closure member of said proportional flow control valve to move to a selected, at least partially closed position, to create a pressure at the proximal end of the endotracheal tube which permits a portion of the flow of gas to flow into said endotracheal tube and the lungs of the patient; and
  causing said valve closure member to thereafter move to a selected, at least partially closed position, to create a pressure within said circulation loop at the proximal end of the endotracheal tube which permits the inspired gas to flow out of the patient's lungs and said endotracheal tube.

77. The method of claim 76 in which said steps of causing a valve closure member to move to said at least partially closed and partially open positions, comprises causing a profiled plug to move toward and away from a discharge opening within the interior of said proportional flow control valve through which said flow of gas from said circulation loop is directed.

78. A method of anesthetizing a patient, comprising:
  circulating a flow of gas containing oxygen and at least one anesthetic within a circulation loop connected to an airway device to which the patient is connected;
  producing a signal in response to the failure of a bellows connected to said circulation loop to return to a baseline position at end expiration;
  introducing additional gas into said recirculation loop in response to production of said signal.

79. The method of claim 78 in which said step of producing a signal comprises sensing the movement of said bellows from said baseline position by operation of a linear optical encoder.

80. The method of claim 79 in which said step of introducing additional gas into said circulation loop comprises opening a first gas make-up valve connected to a source of oxygen, and opening a second gas make-up valve connected to a source of clinical gas.

81. The method of claim 78 in which said step of introducing additional gas further comprises introducing a volatile anesthetic into said circulation loop.

82. A method of anesthetizing a patient, comprising:

circulating a flow of gas containing oxygen and at least one anesthetic within a circulation loop connected to an airway device to which the patient is connected;

transmitting at least a portion of said flow of gas out of said circulation loop and into a scavenging system connected to a vacuum source;

maintaining a substantially constant pressure within said scavenging system independent of any fluctuations in the negative pressure provided by said vacuum source or inflow from the circulation loop into the scavenging system.

83. The method of claim 82 in which said step of maintaining a substantially constant pressure within said scavenging system comprises selectively moving a proportional flow control valve proportionately between an open position and closed position within a scavenger system manifold in response to signals generated by a pressure sensor connected to said manifold.

84. A method of ventilating a patient, comprising:

circulating a flow of gas within a circulation loop and into an airway device communicating with the lungs of a patient;

operating a variable-orifice control device, located within the circulation loop, so that the peak end expiratory pressure in the lungs of the patient does not fall below a selected level above ambient pressure.

85. The method of claim 84 in which said step of operating a variable-orifice control device comprises adjusting a variable-orifice flow device in the course of exhalation by the patient so that a selected pressure above ambient pressure is maintained in the patient's lungs at end exhalation.

86. A method of ventilating a patient, comprising:

circulating a flow of gas within a circulation loop and into an airway device communicating with the lungs of patient;

operating a variable orifice control device, located within the circulation loop, to permit gas within the circulation loop to flow in a direction downstream from the airway device and through the variable orifice control device in the event the pressure at the airway device exceeds a selected maximum level.

87. The method of claim 86 in which said step of operating a variable orifice control device comprises selectively opening the variable orifice control device in the event the pressure at the airway device exceeds a selected maximum level to permit the passage of gas through the variable orifice control device.

88. An apparatus for use as a ventilator and/or an anesthesia delivery system, comprising:

a circulation loop connectable to an airway device to which a patient can be connected;

a blower operative to circulate a flow of intermixed oxygen, a second gas and at least one anesthetic within said circulation loop;

a multi-gas sensor having an input located at a distal tip of an endotracheal tube, said multi-gas sensor being effective to sense the presence of at least oxygen, anesthetic gas and carbon dioxide;

first, second and third supply means for introducing oxygen, the second gas and the at least one anesthetic, respectively, into said circulation loop, said third supply means being a motorized anesthetic syringe pump connected to said circulation loop, said syringe pump including a pump body having an interior carrying a movable plunger, a needle connected at one end to said interior of said pump body, and a sintered metal insert carried within a copper block located in said circulation loop, said needle being connected to said sintered metal insert to deliver liquid anesthetic therein where it is vaporized and carried by said circulation loop to a lung of the patient; and a controller operatively connected to each of said first, second and third supply means and to said multi-gas sensor, said controller being effective upon receipt of signals from said multi-gas sensor to selectively control the operation of said first, second and third supply means to obtain the desired, relative concentration of oxygen, the second gas and said the at least one anesthetic within said circulation loop.

\* \* \* \* \*